United States Patent
Donega et al.

(10) Patent No.: US 11,745,010 B2
(45) Date of Patent: Sep. 5, 2023

(54) NERVE STIMULATION DEVICE FOR CURRENT STEERING

(71) Applicants: Galvani Bioelectronics Limited, Brentford (GB); UCL Business LTD, London (GB)

(72) Inventors: Matteo Donega, Brentford (GB); Daniel Chew, Brentford (GB); David Holder, London (GB); Kirill Aristovich, London (GB)

(73) Assignees: GALVANI BIOELECTRONICS LIMITED, Middlesex (GB); UCL BUSINESS LTD., London (GB)

( * ) Notice: Subject to any disclaimer, the term of this patent is extended or adjusted under 35 U.S.C. 154(b) by 11 days.

(21) Appl. No.: 15/733,277

(22) PCT Filed: Dec. 11, 2018

(86) PCT No.: PCT/GB2018/053600
§ 371 (c)(1),
(2) Date: Jun. 19, 2020

(87) PCT Pub. No.: WO2019/122817
PCT Pub. Date: Jun. 27, 2019

(65) Prior Publication Data
US 2020/0384265 A1    Dec. 10, 2020

Related U.S. Application Data

(60) Provisional application No. 62/609,223, filed on Dec. 21, 2017.

(51) Int. Cl.
*A61N 1/05* (2006.01)
*A61N 1/36* (2006.01)

(52) U.S. Cl.
CPC ....... *A61N 1/0556* (2013.01); *A61N 1/36053* (2013.01); *A61N 1/36135* (2013.01);
(Continued)

(58) Field of Classification Search
None
See application file for complete search history.

(56) References Cited

U.S. PATENT DOCUMENTS 5,400,784 A   3/1995  Durand et al.
5,919,220 A   7/1999  Stieglitz et al.
(Continued)

FOREIGN PATENT DOCUMENTS

DE         4433111 A1    3/1996
DE    102014014927 A1    4/2016
(Continued)

OTHER PUBLICATIONS

Honert C V D., et al., "Generation of Unidirectionally Propagated Action Potentials in a Peripheral Nerve by Brief Stimuli," Science, vol. 206, No. 4424, Dec. 14, 1979, pp. 1311-1312.
(Continued)

*Primary Examiner* — Catherine M Voorhees
*Assistant Examiner* — Elizabeth K So
(74) *Attorney, Agent, or Firm* — Merchant & Gould P.C.

(57) ABSTRACT

A nerve stimulation system including at least one nerve interface device is disclosed. The device includes a cuff portion having an assembled position in which the cuff portion forms at least part of a passageway for receiving a nerve along a longitudinal axis passing through the passageway; and first and second rings of electrodes mounted on the cuff portion, each ring of electrodes including a plurality of electrodes, and wherein each electrode in the first ring has a corresponding longitudinally-aligned electrode in the second ring so as to form a plurality of pairs of electrodes
(Continued)

spaced apart from each other along the longitudinal axis. The system includes a stimulation device in communication with the pairs of electrodes to generate different electrical signals for the pairs of electrodes and a control system that causes the different signals to causes different physiological responses.

3 Claims, 21 Drawing Sheets

(52) U.S. Cl.
CPC ........ *A61N 1/36167* (2013.01); *A61N 1/3611* (2013.01); *A61N 1/36114* (2013.01)

(56) References Cited

U.S. PATENT DOCUMENTS

| | | | |
|---|---|---|---|
| 6,480,743 | B1 | 11/2002 | Kirkpatrick et al. |
| 9,314,637 | B2 | 4/2016 | Libbus |
| 2003/0045909 | A1 | 3/2003 | Gross et al. |
| 2003/0050677 | A1* | 3/2003 | Gross ................. A61N 1/36071 607/72 |
| 2004/0015204 | A1 | 1/2004 | Whitehurst et al. |
| 2006/0136024 | A1 | 6/2006 | Cohen et al. |
| 2007/0129780 | A1 | 6/2007 | Whitehurst et al. |
| 2008/0243196 | A1 | 10/2008 | Libbus et al. |
| 2011/0160795 | A1 | 6/2011 | Osorio |
| 2013/0005169 | A1 | 1/2013 | Soltis et al. |
| 2013/0172774 | A1 | 7/2013 | Crowder et al. |
| 2014/0046407 | A1 | 2/2014 | Ben-Ezra et al. |
| 2014/0214135 | A1 | 7/2014 | Ben-David et al. |
| 2014/0228905 | A1 | 8/2014 | Bolea |
| 2015/0134031 | A1 | 5/2015 | Moffitt et al. |
| 2015/0202433 | A1 | 7/2015 | Franke et al. |
| 2015/0321000 | A1 | 11/2015 | Rosenbluth et al. |
| 2016/0199651 | A1 | 7/2016 | Meadows et al. |
| 2016/0263376 | A1* | 9/2016 | Yoo .................... A61N 1/36017 |
| 2016/0310741 | A1 | 10/2016 | Baru et al. |
| 2016/0331975 | A1 | 11/2016 | Henry et al. |
| 2017/0202467 | A1 | 7/2017 | Zitnik et al. |
| 2018/0161570 | A1 | 6/2018 | Renaux |
| 2020/0316372 | A1 | 10/2020 | Bashirullah et al. |
| 2021/0093867 | A1 | 4/2021 | Donega et al. |
| 2021/0093868 | A1 | 4/2021 | Hunsberger |
| 2021/0138238 | A1 | 5/2021 | Holder et al. |

FOREIGN PATENT DOCUMENTS

| | | |
|---|---|---|
| GB | 2528070 A | 1/2016 |
| KR | 20120077585 A | 7/2012 |
| WO | WO-2008007065 A2 | 1/2008 |
| WO | WO-2008142027 A1 | 11/2008 |

OTHER PUBLICATIONS

Honert V. D.C., et al., "A Technique for Collision Block of Peripheral Nerve:Frequency Dependence,", IEEE Transactions on Biomedical Engineering, May 1981, vol. BME-28, No. 5, 4 pages.
International Preliminary Report on Patentability for Application No. PCT/GB2018/051749, dated Dec. 24, 2019, 9 pages.
International Preliminary Report on Patentability for Application No. PCT/GB2018/053597, dated Jun. 25, 2020, 9 pages.
International Preliminary Report on Patentability for Application No. PCT/GB2018/053600, dated Jun. 23, 2020, 8 pages.
International Preliminary Reporton Patentability for Application No. PCT/GB2018/053601, dated Jun. 23, 2020, 7 pages.
International Preliminary Report on Patentability for Application No. PCT/GB2018/053602, dated Jun. 23, 2020, 11 pages.
International Search Report and Written Opinion for Application No. PCT/GB2018/051749, dated Oct. 11, 2018, 13 pages.
International Search Report and Written Opinion for Application No. PCT/GB2018/053600, dated Mar. 22, 2019, 12 pages.
International Search Report and Written Opinion for Application No. PCT/GB2018/053601, dated Feb. 12, 2019, 10 pages.
International Search Report and Written Opinion for Application No. PCT/GB2018/053602, dated Feb. 13, 2019, 15 pages.
International Search Report and Written Opinion, International Application No. PCT/GB2018/053597, dated Jul. 17, 2019, 12 pages.
Sweeney J D., et al., "An Asymmetric Two Electrode Cuff for Generation of Unidirectional Propagated Action Potentials," IEEE Transactions on Biomedical Engineering, Jun. 1986, vol. 33, No. 6, pp. 541-549.

* cited by examiner

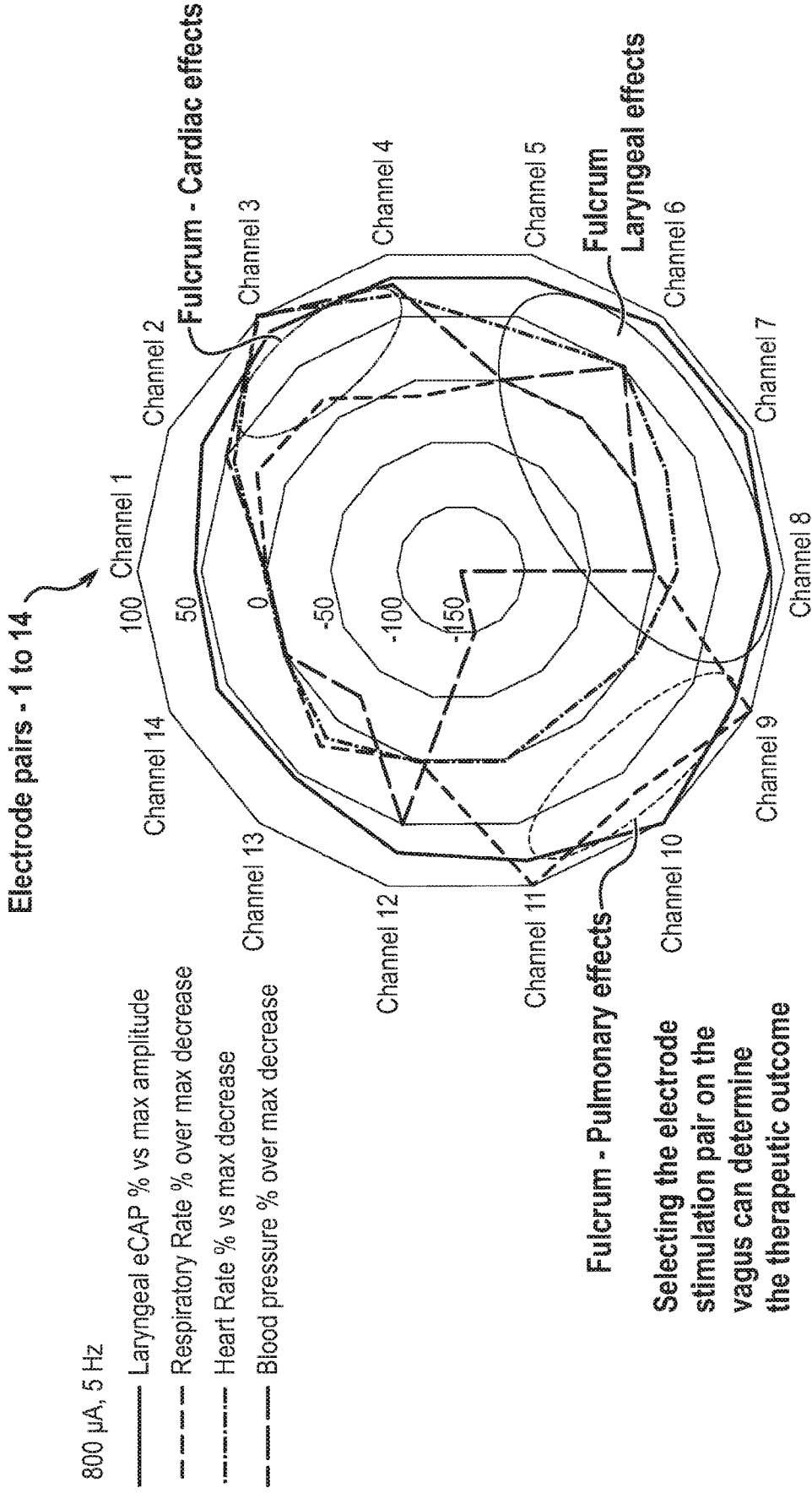

1mm array

FIG. 3b(contd.)
3mm array
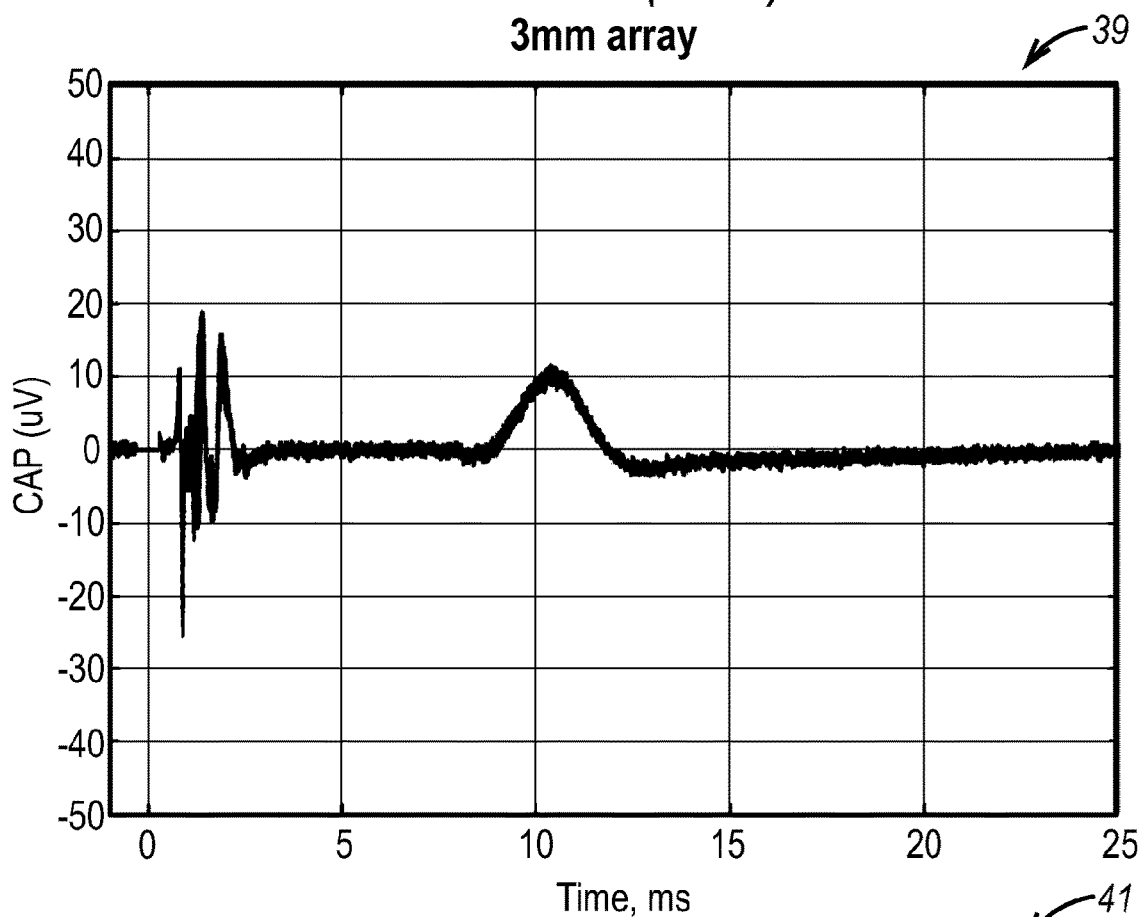
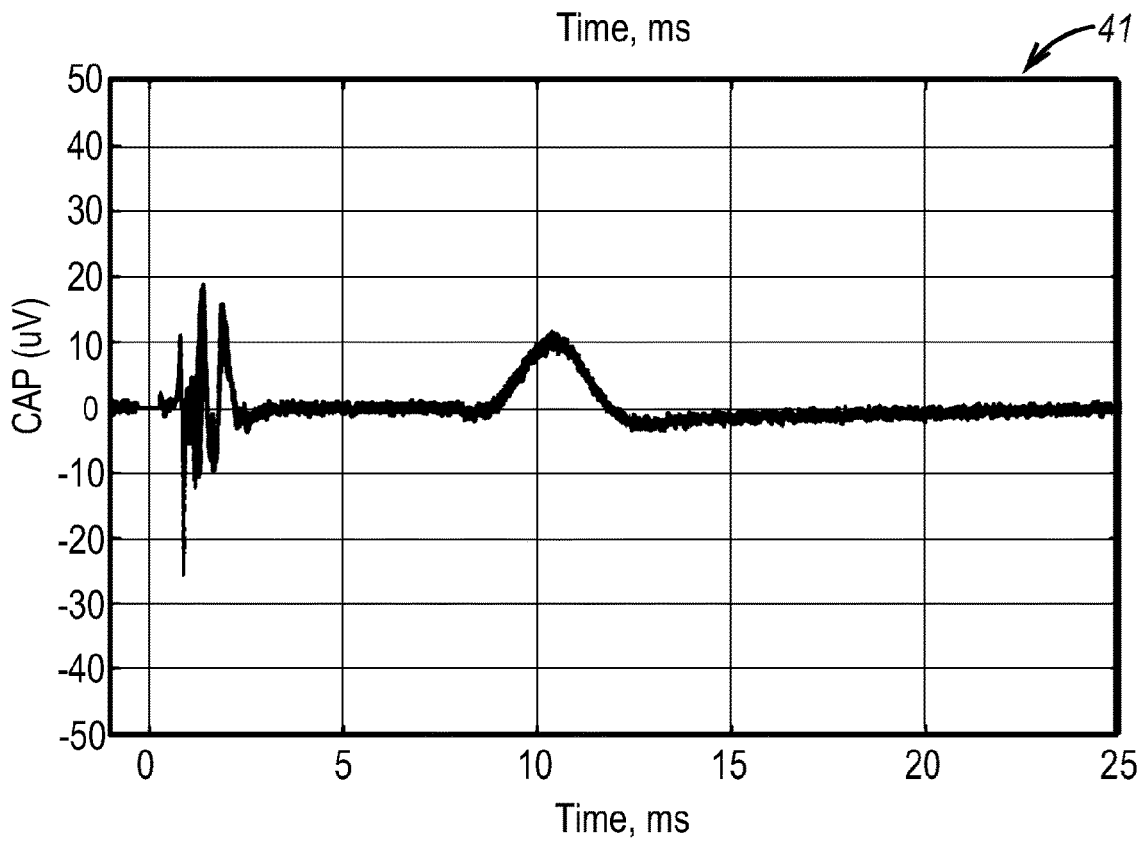

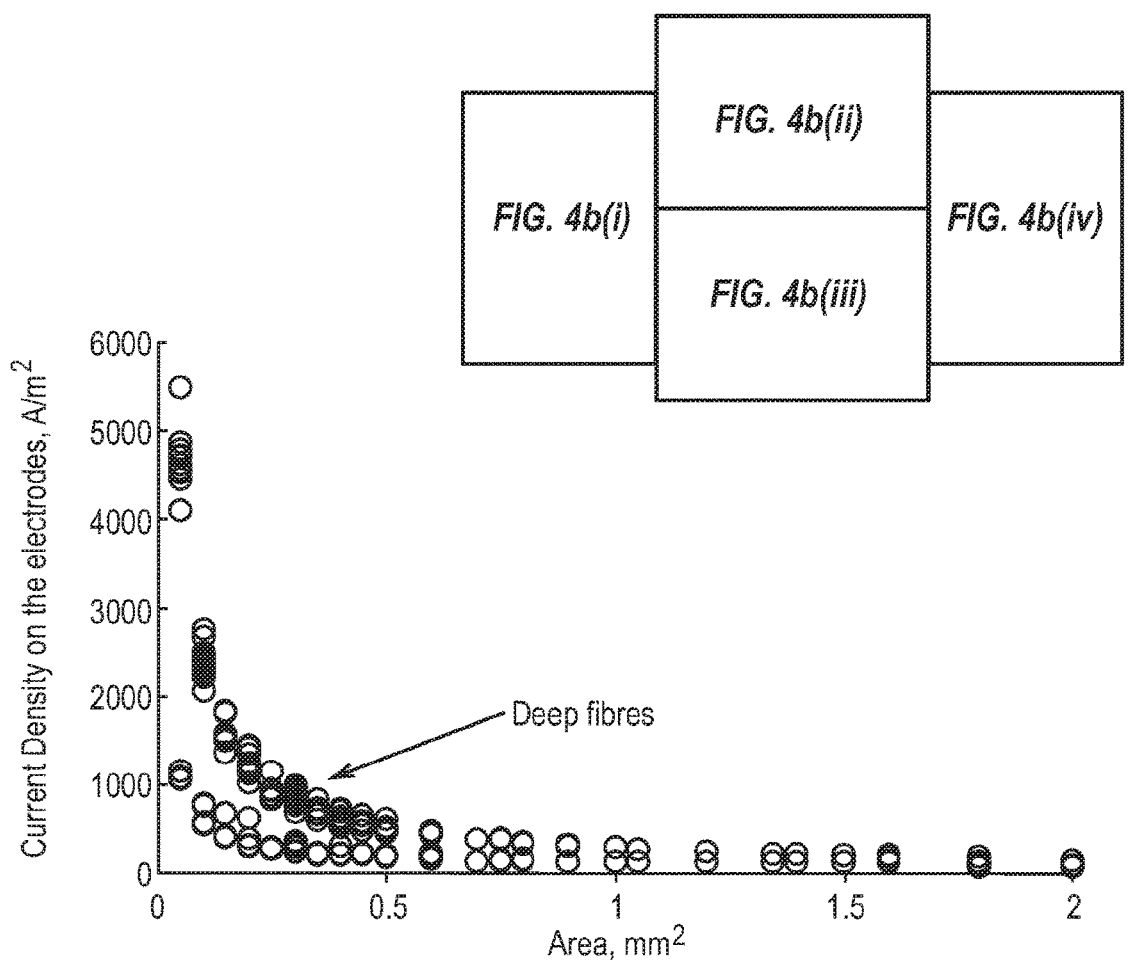
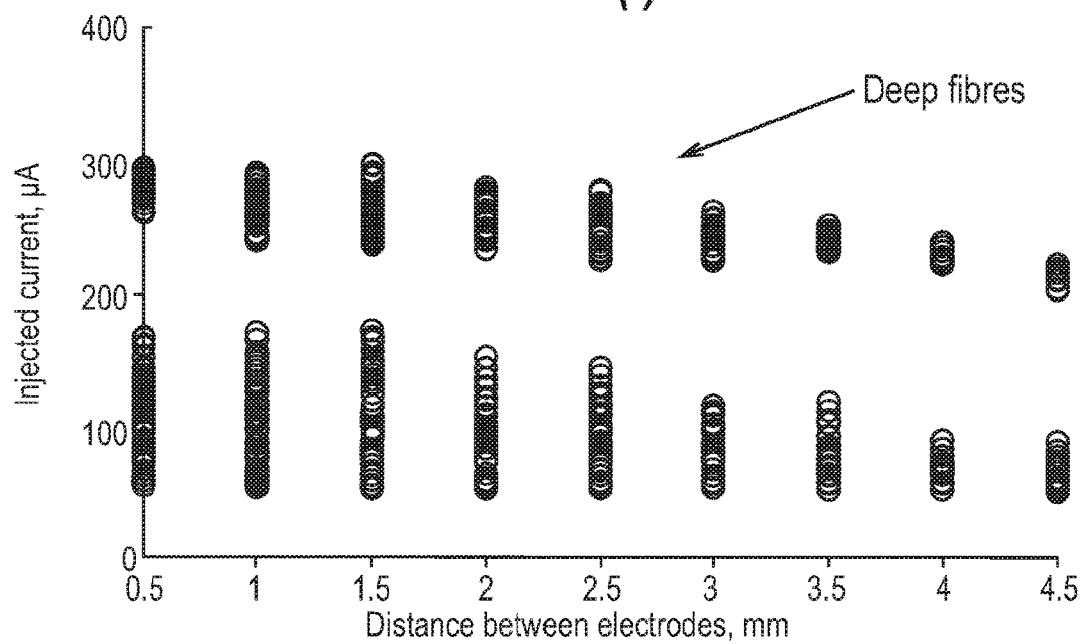

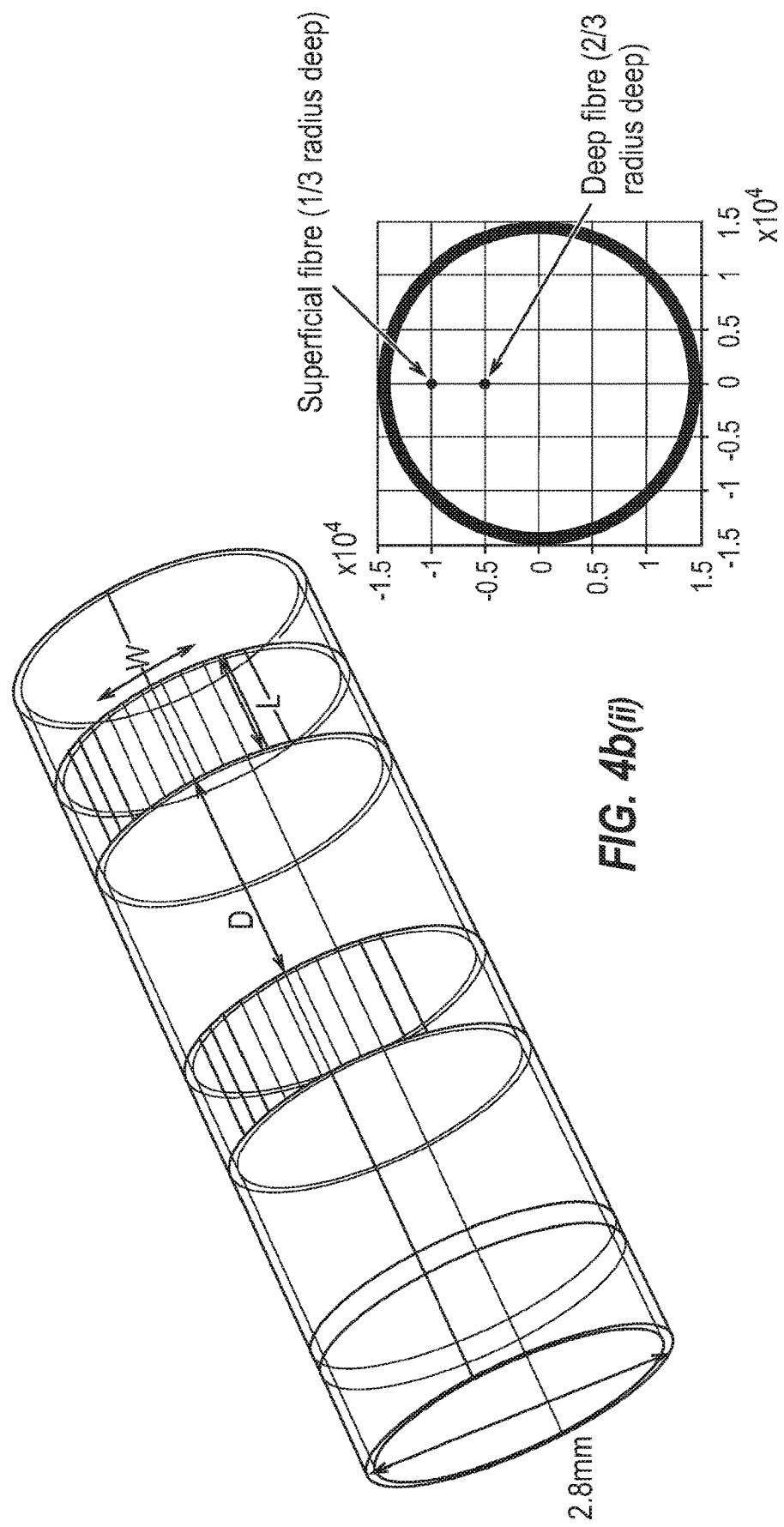
FIG. 4b(ii)

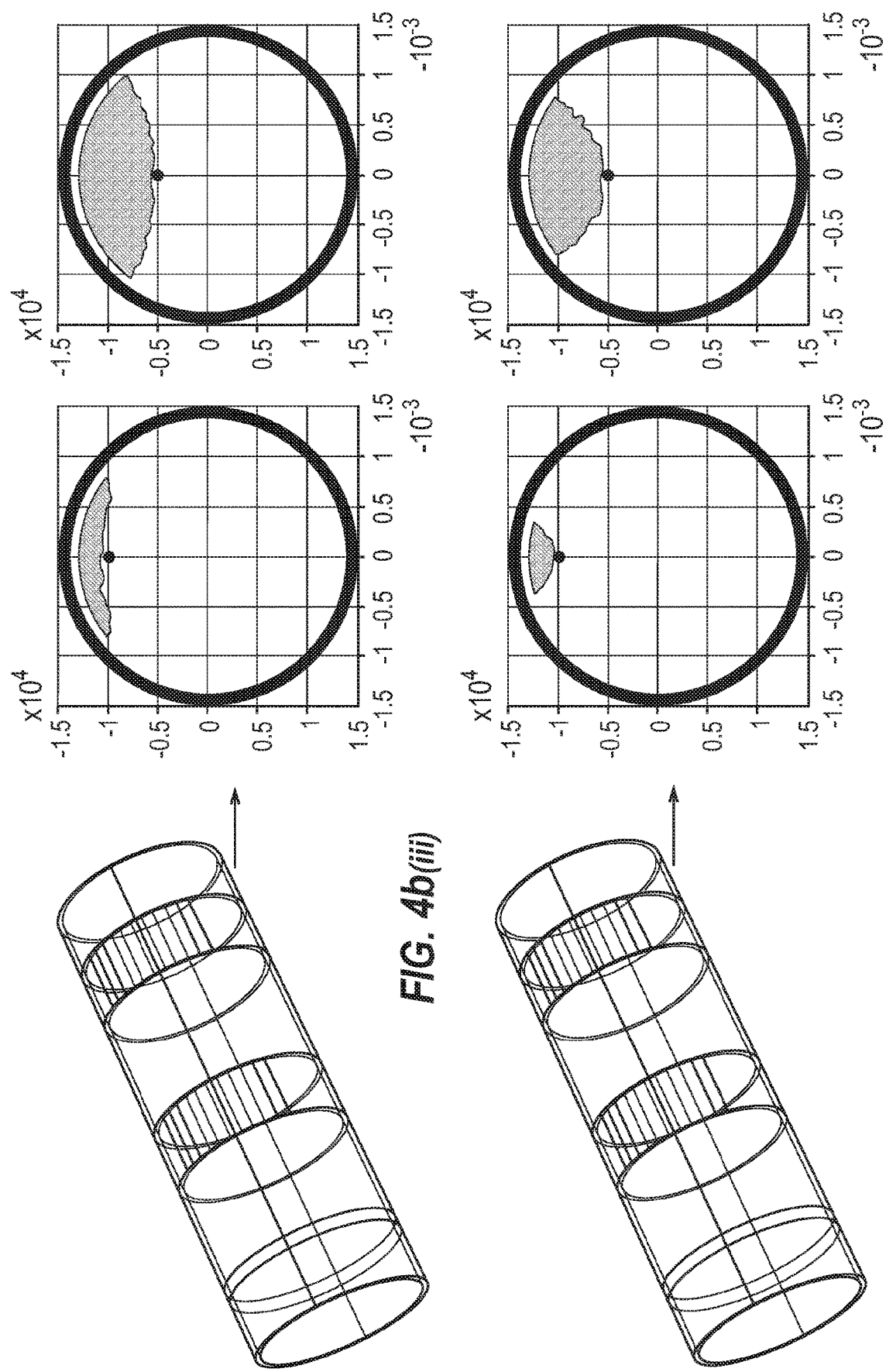
FIG. 4b(iii)

FIG. 4b(iv)
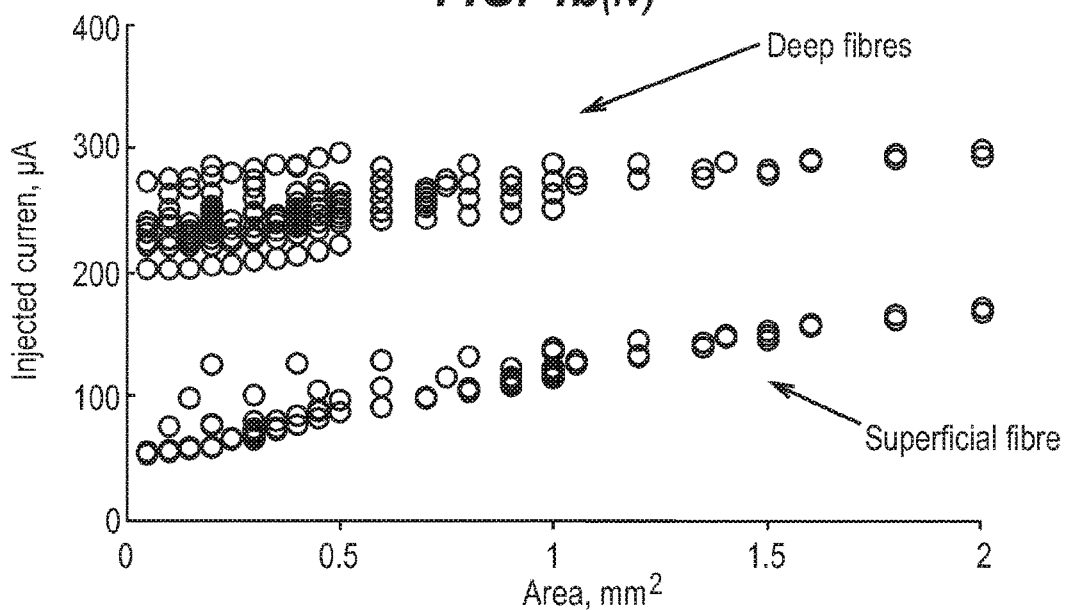
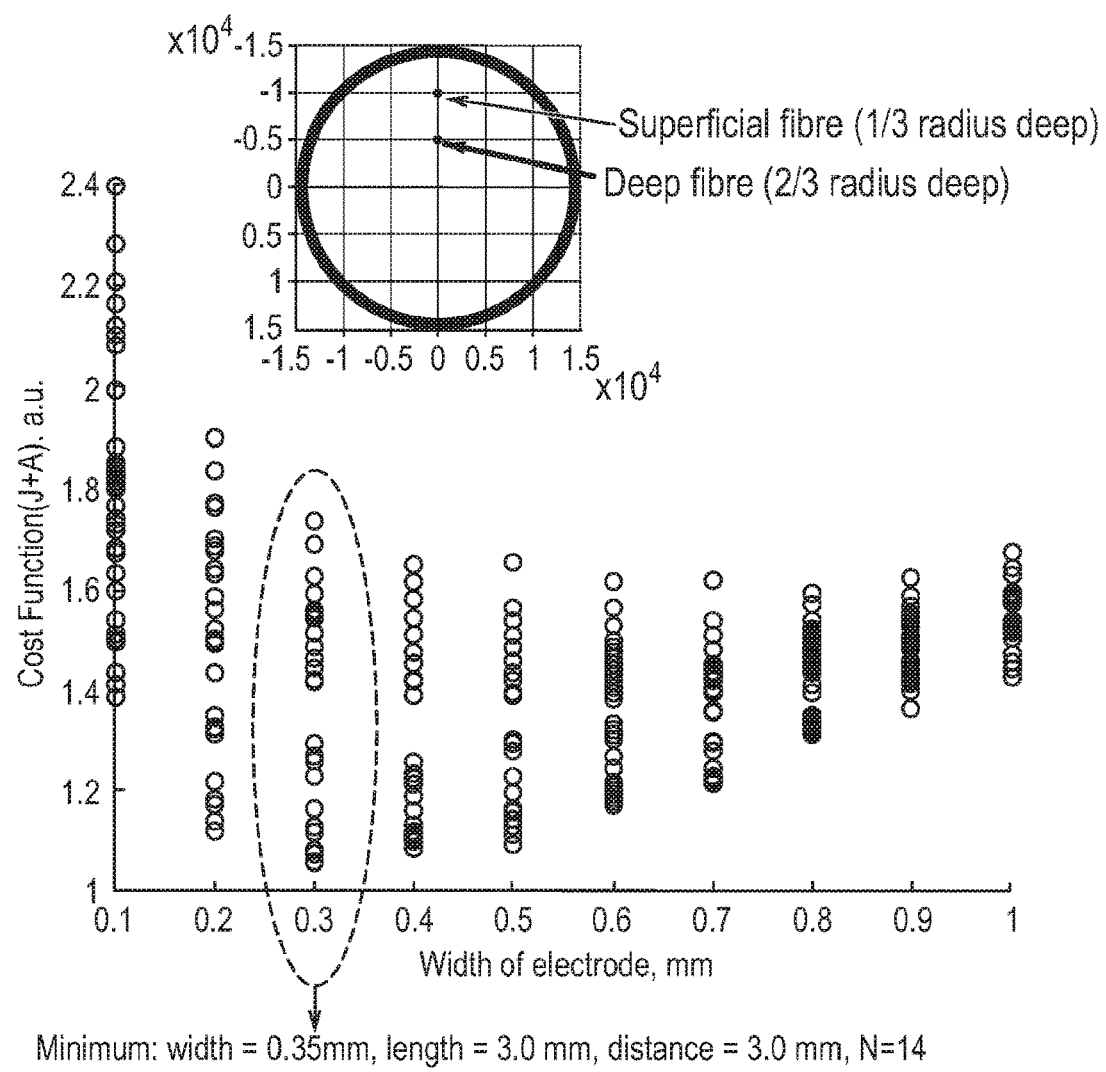
Minimum: width = 0.35mm, length = 3.0 mm, distance = 3.0 mm, N=14

Pair = 1-1

Pair = 2-2

Pair = 3-3

Pair = 4-4

Pair = 5-5

Pair = 6-6

Pair = 7-7

Pair = 8-8

Pair = 9-9

Pair = 10-10

Pair = 11-11

Pair = 12-12

Pair = 13-13

Pair = 14-14

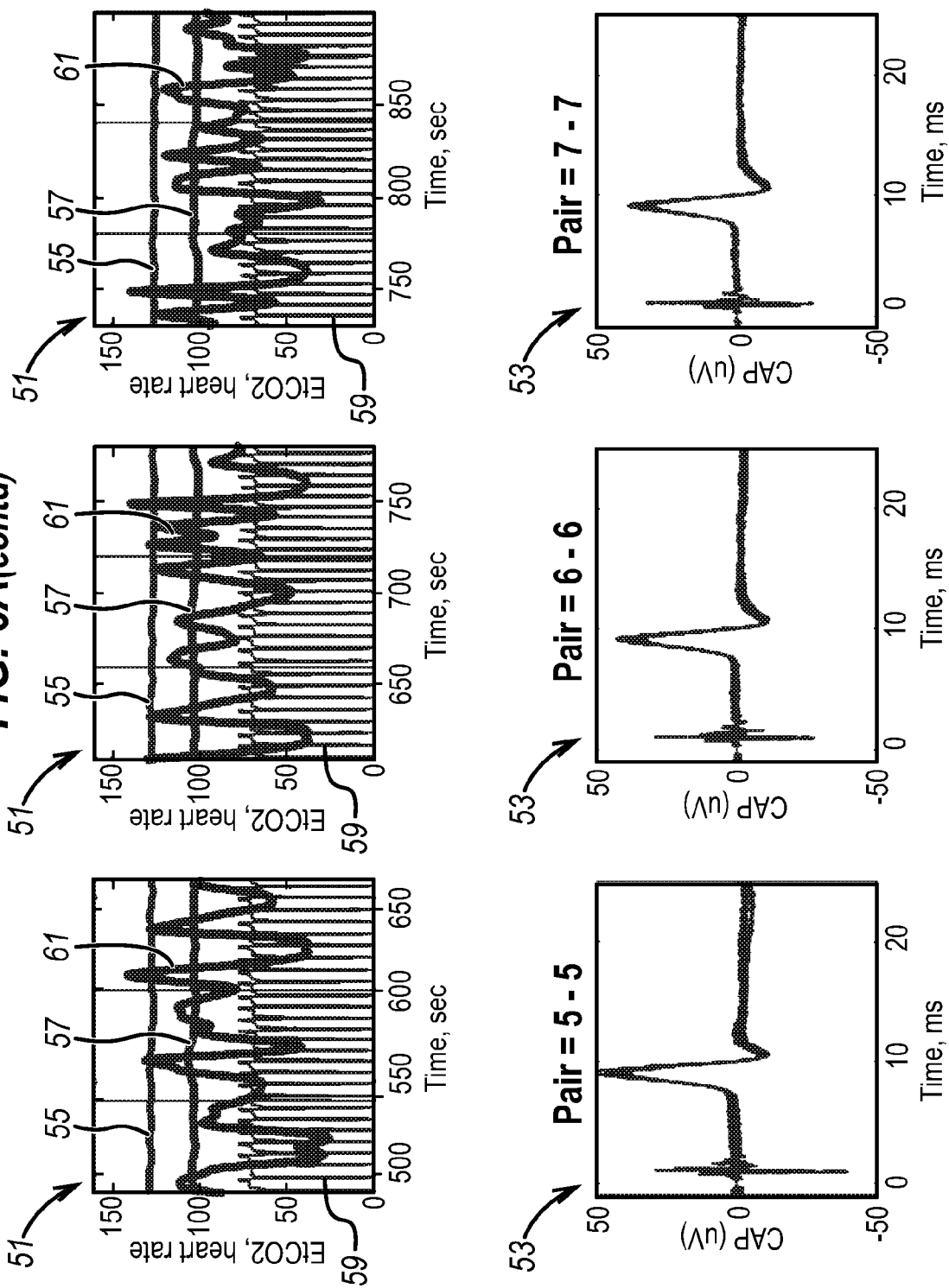

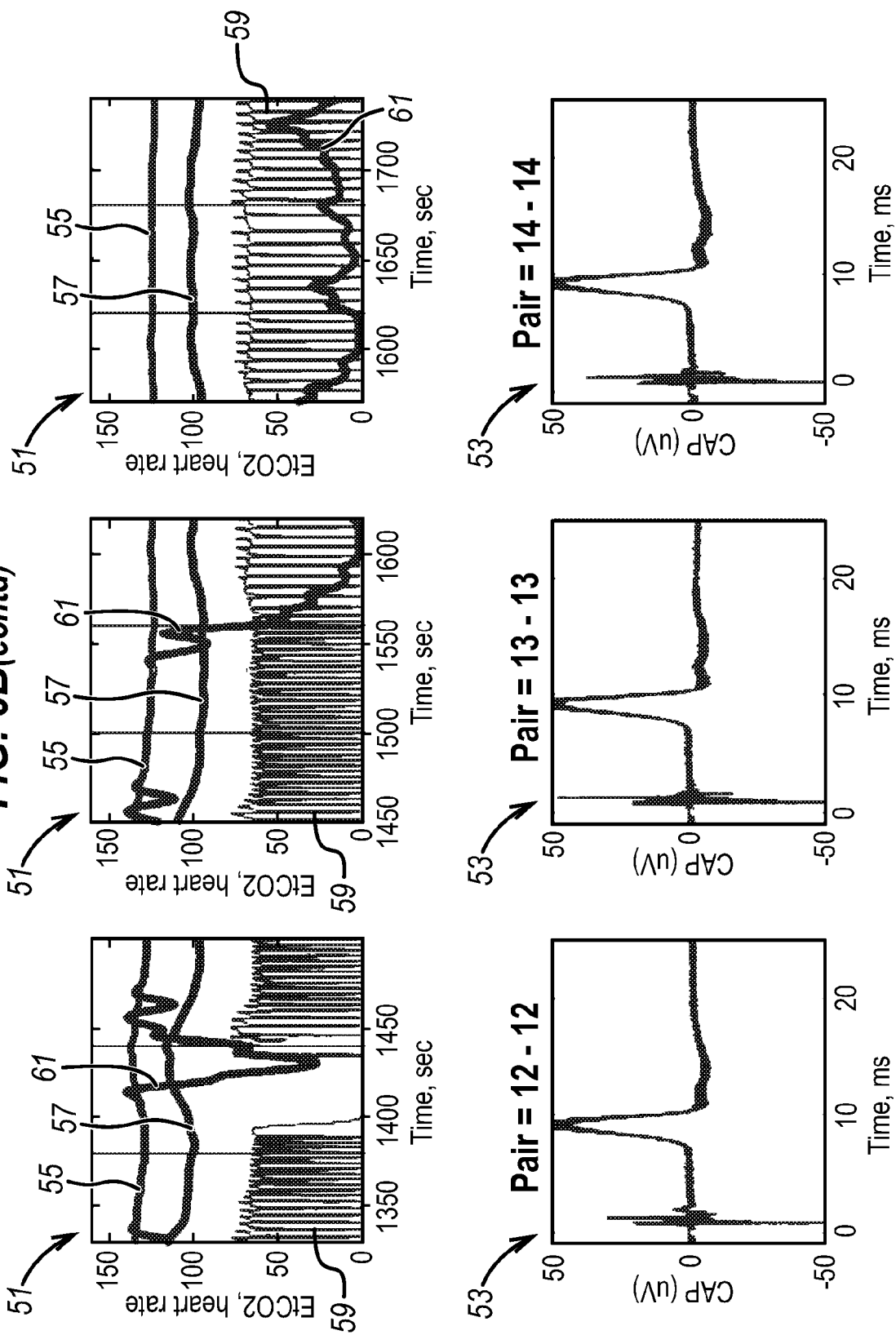
FIG. 6B(contd)

NERVE STIMULATION DEVICE FOR CURRENT STEERING

PRIORITY CLAIM

The present application is a National Phase entry of PCT Application No. PCT/GB2018/053600, filed Dec. 11, 2018, which claims priority from U.S. Provisional Application No. 62/609,223, filed Dec. 21, 2017, each of which is hereby fully incorporated herein by reference.

TECHNICAL FIELD

This disclosure relates to a system, a method and a computer program for stimulating a nerve.

BACKGROUND

It is desirable to be able to selectively stimulate bundles of nerves or fascicles, within a complex nerve, which are specific to certain organs. This may allow certain responses in specific organs to be induced. The vagus nerve is an example of a complex nerve, and it is known that different fascicles within the vagus nerve may be stimulated in order to induce certain responses in different organs.

The desire to selectively stimulate bundles of nerves or fascicles, within a complex nerve, follows on from research that allows for the identification of organ specific fibers within a peripheral nerve. One known method for this involves inserting an electrode array with penetrating shanks into the nerve and recording local field potentials. The correlation of the recording of spontaneous local field potentials with physiological activity, such as ECG and respiration, allows the position of organ specific bundles to be determined. This known method has drawbacks because the insertion of electrodes into the nerve may result in the damage of fibers. This has potentially serious consequences.

Selective stimulation of specific fiber types within a mixed nerve (including myelinated and unmyelinated fibers) could provide higher specificity and lower side effects when targeting specific types of fibers to cause specific physiological responses. However, this can be difficult to achieve with known electrodes assemblies, such as the electrode ring described in WO 2016/170327. Furthermore, selective stimulation using penetrative electrodes is undesirable as outlined above.

It is known that different geometries of electrode are capable of stimulating different fiber types.

Furthermore, there is a desire for treatment by neural stimulation to be as minimally invasive as possible. Hitherto, treatment of multiple diseases by neural stimulation involved implanting a neural stimulation system for each treatment. Particularly in situations where such treatment takes place on the same nerve, particularly a complex nerve, such that available space is highly restricted, the use of multiple neural stimulation systems can be problematic. There is therefore a desire for more compact and less invasive neural stimulation systems, particularly for treatment of multiple diseases, particularly on complex nerves.

SUMMARY

In a first aspect, the present disclosure provides a nerve stimulation system comprising at least one nerve interface device. The device comprises at least one cuff portion having an assembled position in which the cuff portion forms at least part of a passageway for receiving a nerve along a longitudinal axis passing through the passageway; and first and second rings of electrodes mounted on the at least one cuff portion, each ring of electrodes comprising a plurality of electrodes, and wherein each electrode in the first ring has a corresponding longitudinally-aligned electrode in the second ring so as to form a plurality of pairs of electrodes spaced apart from each other along the longitudinal axis. The plurality of pairs of electrodes includes at least a first pair of electrodes and a second pair of electrodes, the first pair of electrodes mounted on the at least one cuff portion at a different circumferential position to the second pair of electrodes. The system further comprises a stimulation device in electrical communication with the first and second pairs of electrodes and configured to generate first and second electrical signals, the first electrical signal being different from the second electrical signal with respect to at least one signal parameter. The system further comprises a control system configured to cause the stimulation device to deliver the first electrical signal to the first pair of electrodes for causing a first physiological response and to deliver the second electrical signal to the second pair of electrodes for causing a second physiological response that is different from the first physiological response.

The second physiological response can be complementary to the first in that it will avoid or reduce the effect of the first physiological response. This allows the system to be selective in delivering treatments of certain diseases via particular neural pathways, but also allows off target effects that are typical in such treatments to be avoided.

By delivering different signals to different pairs of electrodes circumferentially spaced around the cuff (and therefore circumferentially spaced around, for example, a complex nerve) it is possible to treat multiple diseases by delivering multiple signals to a corresponding multiple bundles of nerves or fascicles within the complex nerve via corresponding multiple pairs of electrodes. Signals may be 'different' if they differ in at least one parameter, and it may be that a parameter of the second signal is reduced with respect to a corresponding parameter of the first.

In a second aspect, the present disclosure provides a nerve stimulation system comprising at least one nerve interface device. The device comprises at least one cuff portion having an assembled position in which the cuff portion forms at least part of a passageway for receiving a nerve along a longitudinal axis passing through the passageway; and first and second rings of electrodes mounted on the at least one cuff portion, each ring of electrodes comprising a plurality of electrodes, and wherein each electrode in the first ring has a corresponding longitudinally-aligned electrode in the second ring so as to form a plurality of pairs of electrodes spaced apart from each other along the longitudinal axis. The plurality of pairs of electrodes comprise a first subset of pairs of electrodes and a second subset of pairs of electrodes, wherein one or both electrodes in each pair of electrodes in the first subset has a first geometry, and wherein one or both electrodes in each pair of electrodes in the second subset has a second geometry different from the first. The system further comprises a stimulation device in electrical communication with the plurality of pairs of electrodes and configured to generate at least one electrical signal. The system further comprises a control system configured to cause the stimulation device to deliver the at least one electrical signal to one or more pairs of electrodes in the first subset for stimulating a myelinated fiber, and/or to deliver the at least one electrical signal to one or more pairs of electrodes in the second subset for stimulating an unmyelinated fiber.

By delivering one or more signals using subsets of electrode pairs circumferentially spaced around the cuff (and therefore circumferentially spaced around, for example, a complex nerve), wherein the subsets differ in the geometry of one or both electrodes in the pairs, it is possible to target different fiber types in the bundles of nerves or fascicles within the complex nerve.

In another aspect, the present disclosure provides a computer program comprising code portions which when loaded and run on a computing device within the control system of the nerve stimulation system of a system according to the first aspect, cause the control system to stimulate the first pair of electrodes of the nerve stimulation system to provide a first electrical signal to the first pair of electrodes, and stimulate the second pair of electrodes of the nerve stimulation system to provide a second electrical signal, different from the first electrical signal, to the second pair of electrodes.

In another aspect, the present disclosure provides a computer program comprising code portions which when loaded and run on a computing device within the control system of the nerve stimulation system of a system according to the second aspect, cause the control system to stimulate a first pair of electrodes in the first subset of pairs of electrodes of the nerve stimulation system and stimulate a second pair of electrodes in the second subset of pairs of electrodes of the nerve stimulation system.

In another aspect, the present disclosure provides a nerve stimulation method comprising: providing a nerve stimulation system according to the first aspect; stimulating the first pair of electrodes to provide a first electrical signal to the first pair of electrodes; and stimulating the second pair of electrodes to provide a second electrical signal, different from the first electrical signal, to the second pair of electrodes.

In another aspect, the present disclosure provides a nerve stimulation method comprising: providing a nerve stimulation system according to the second aspect; stimulating a first pair of electrodes in the first subset of pairs of electrodes of the nerve stimulation system; and stimulating a second pair of electrodes in the second subset of pairs of electrodes of the nerve stimulation system.

BRIEF DESCRIPTION OF THE DRAWINGS

Embodiments of the disclosure will be described, by way of example, with reference to the following drawings, in which:

FIG. 3a illustrates an embodiment of application of nerve stimulation devices according to the present disclosure and FIG. 3b illustrates measurements of compound action potentials (CAP) measured in response to stimulation of a nerve using the nerve stimulation devices.

FIG. 4B illustrates radially located "virtual fascicles".

DETAILED DESCRIPTION

Described herein is a device, system and method that allows multiple specific nerve fibers to be selectively stimulated within a complex nerve such as the vagus nerve. This enables fibers to be targeted more precisely thereby treating diseases more effectively while avoiding off target effects, and enables treatment of multiple diseases.

For example, specific stimulation of pulmonary bundles of the vagus nerve could help treat asthma and other respiratory conditions, whilst avoiding side-effects on other organs. Alternatively, selective stimulation of descending c-fiber bundles could optimize the stimulation of visceral organs, without affecting the cardio-respiratory system. Also, selective stimulation could be used to avoid contraction of the thyroarytenoid (TA) muscle of the larynx, which is the most common and serious side-effect of current vagus nerve stimulators used to treat inflammatory diseases. This system may be provided in an implantable device.

Figure 1:
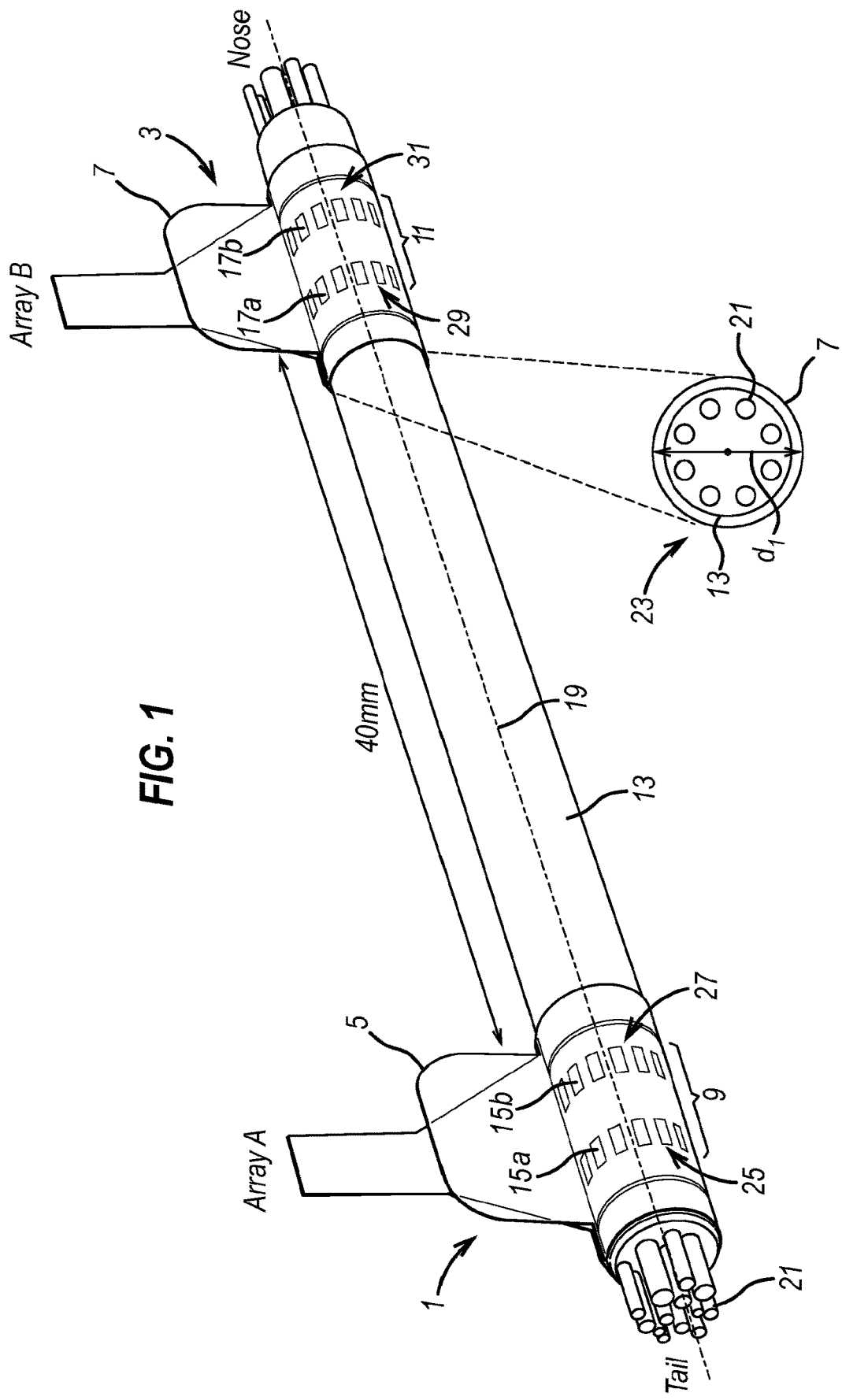
FIG. 1 illustrates examples of a nerve stimulation device.

Referring to FIG. 1, there is provided a first nerve stimulation device 1 (otherwise referred to as electrode array "A") and a second nerve stimulation device 3 (otherwise referred to as electrode array "B"). Each one of the arrays 1, 3 comprises a cuff portion 5, 7 upon which is provided a plurality of electrodes 9, 11. The provision of two devices 1, 3 is not essential and the benefits of the disclosure may be realized with just one.

The cuff portion 5, 7 is a flexible sheet with the electrodes 9, 11 mounted on the sheet. The sheet can be wrapped around a nerve of a subject 13, such that the electrodes 9, 11 form an electrical contact with the nerve at various points around the surface of the nerve 13. When the cuff is wrapped around the nerve 11, in its assembled position, the cuff forms an aperture (or tubular section/passageway) for receiving the nerve 13. As illustrated, the cuff 5, 7 receives the nerve along a cuff axis 19 (or longitudinal axis) which passes through the middle of the cuff 5, 7. This cuff axis 19 is also the longitudinal axis of the nerve 13.

As illustrated, in use the arrays 1, 3 can be separated from one another along the length of the nerve 13. In this example, the arrays 1, 3 are separated by a distance of 40 mm.

The electrodes may comprise stainless steel and can be fabricated by laser cutting the electrodes into a film. In one example, the film comprises silicon. However, other materials are also possible and equally effective.

As illustrated in the expanded cross-sectional view 23, the aperture formed by the cuff 7 has a diameter (d1). The cuff axis 19 is perpendicular to the diameter and parallel with the depth of the aperture. In other words, the cuff axis is parallel with the depth of the tubular section. Furthermore, the pair of electrodes are offset from one another in a direction perpendicular to the diameter of the aperture and parallel with the depth of the aperture.

Each one of the arrays 1, 3 comprises a plurality of pairs of electrodes 15, 17. These electrode pairs 15, 17 are offset, or spaced apart, from one another in the direction of the cuff axis 19. Thus, the stimulation device can apply a signal to an electrode pair 15, 17 and induce a signal between the electrodes in the pair 15, 17 in a longitudinal direction along the nerve 11. In this way, an electrical channel is provided in the direction of the longitudinal axis 19 of the nerve. This can be used to stimulate specific nerve fibers 21 in the nerve 13, which may be associated with specific organs or physiological responses in the subject.

In this example, the plurality of electrodes in each array 1, 3 are mounted on the same cuff 5, 7. However, it may be possible to provide more than one cuff portion, with some electrode(s) provided on one cuff portion and some electrode(s) provided on another cuff portion.

Each one of the arrays 1, 3 comprises a first set of electrodes 25, 29 and a second set of electrodes 27, 31 mounted on the cuff portion. In the assembled position, the electrodes of first set of electrodes 25, 29 are mounted offset from one another in a direction perpendicular to the cuff axis; and the electrodes of second set of electrodes 27, 31 are mounted offset from one another in a direction perpendicular to the cuff axis 19. As illustrated, the electrodes of the first set of electrodes 25, 29 and the second set of electrodes 27, 31 are spaced in a ring around a circumference of the cuff 5, 7.

The electrodes of the first set of electrodes 25, 29 comprise a first electrode in a pair electrodes 15, 17, and the electrodes of the second set of electrodes 27, 31 comprise a second electrode in the pair 15, 17. The electrodes in each pair 15, 17 are offset from one another along the length of the nerve 11.

In each array 1, 3 the first set 25, 29 and/or the second set 27, 31 of electrodes may comprise 4 to 96 electrodes. However, in a specific example illustrated in FIG. 2, the first set of electrodes 25 and the second set of electrodes 27 of the first array 1 comprises 14 electrodes. Also, the first set of electrodes 25 and the second set of electrodes 27 of the second array 3 comprises 14 electrodes. As illustrated, each set of electrodes 25, 27, 29, 31 comprises a plurality of electrodes arranged sequentially to form a straight line of electrodes on the cuff sheet.

Figure 2:
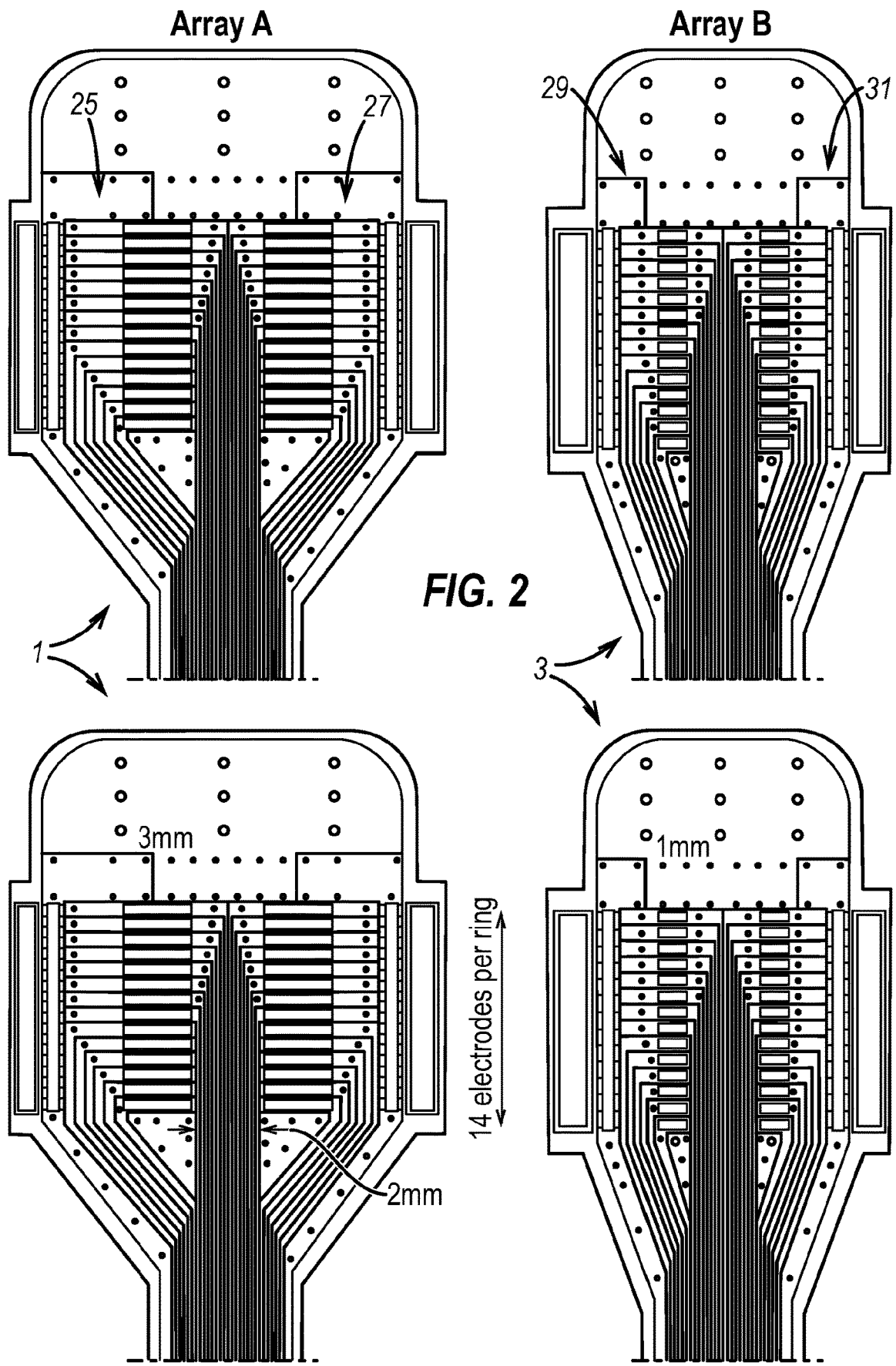
FIG. 2 illustrates schematic representations of the nerve stimulation devices.

FIG. 2 illustrates two schematic views of each of the electrode arrays 1, 3. Each of the electrodes in the arrays 1, 3 have a surface for making electrical contact with the nerve 13. In the first array 1, this surface is rectangular with a width of 0.2 mm and a length of 3 mm. In the second array 3, the surface is also rectangular with a width of 0.2 mm and a length of 1 mm. In another example array (not shown), each of the electrodes has a square surface. This square surface may be 0.2 mm wide and 0.2 mm long. In other words, the length is in the direction parallel to a longitudinal axis of a nerve and the width is in the direction perpendicular to a longitudinal axis of a nerve.

In each of the arrays 1, 3 illustrated in FIG. 2, the electrodes are paired. Each electrode in the first set 25, 29 is paired with an opposing electrode in the second set 27, 31. In the example illustrated, the electrodes in each pair are offset from one another by a distance of 3 mm. Thus, the first set of electrodes 25, 29 is offset from the second set of electrodes 29, 31 by a distance of 3 mm. This distance is measured in the direction of the cuff axis 19.

It will be appreciated that other distances between pairs/sets of electrodes could be used. For instance, the electrode pairs/sets may be offset from one another by a distance of 2 mm. In another example, the electrode pairs/sets may be offset from one another by a distance of 1 mm.

One or more of the arrays 1, 3 may be provided in a nerve stimulation system comprising a stimulation device (not shown) arranged to generate an electrical signal. In this example, the stimulation device is arranged for electrical communication with the first pair of electrodes 15, 17 or each of the plurality of pairs of electrodes of the first device. In this way, the stimulation device can provide an electrical signal to pairs of electrodes.

The stimulation device is capable of generating electrical signals with a variety of different properties. For example, the stimulation device may be arranged to generate signals each with a different pulse duration, frequency, pulse width and current. In addition, the stimulation device may be capable of generating a bipolar pulse.

In one example, the signal has a pulse width of 1 ms. The signal may have a frequency of 1-50 Hz frequency. More specifically, the signal may have a frequency of 2 Hz. The signal may have a pulse width of 50-2000 μs. A pulse width refers to a width of a full pulse. A pulse duration refers to the time period during which the pulse is applied for or delivered for. The amplitude of the current of the signal may be between 100 μA-50 mA.

In another example, the signal has a current of 500 μA, a pulse width of 0.1 ms and/or a frequency of 5 Hz. In yet another example, the signal has a frequency of 20 Hz and/or a duration of 60 seconds.

Figure 1A:
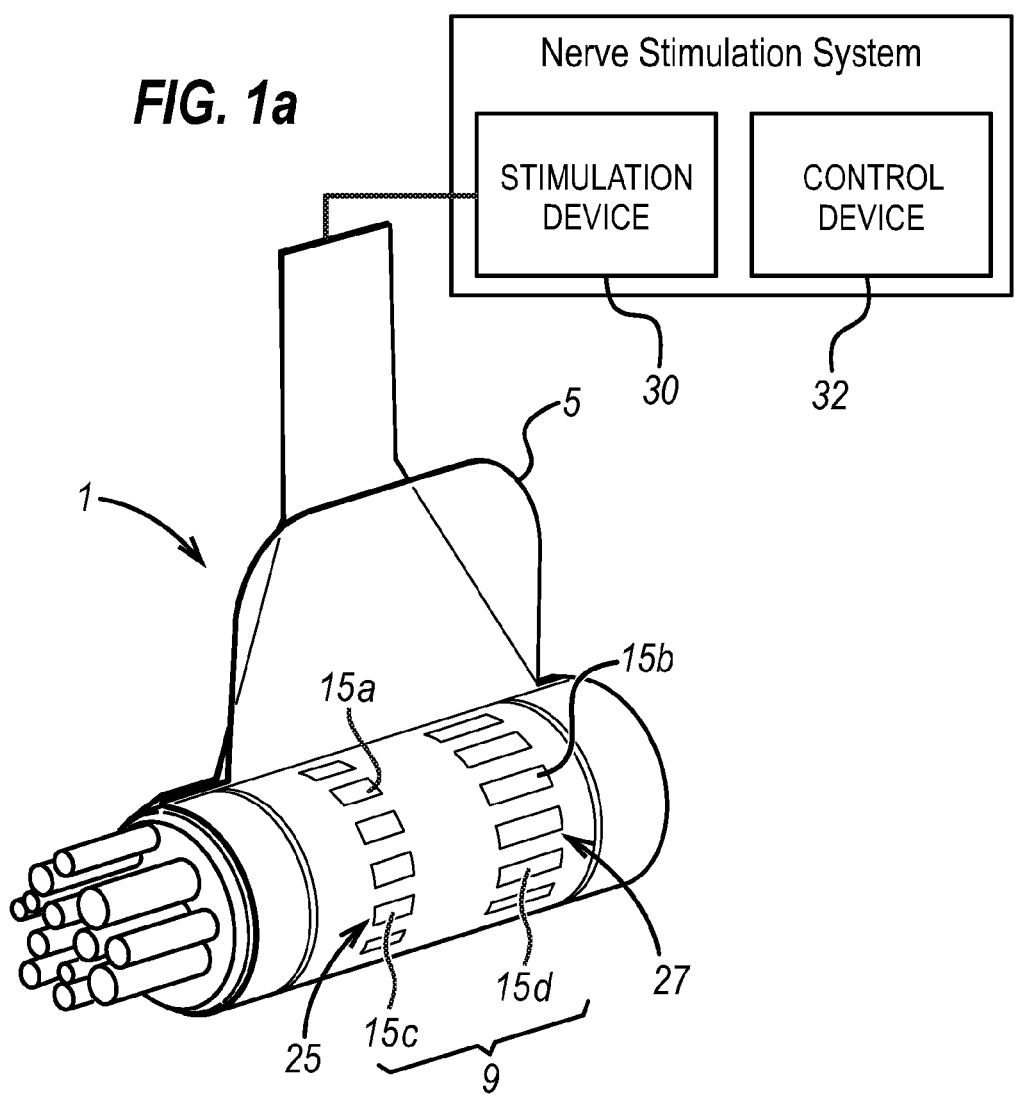
FIG. 1a illustrates a schematic diagram of components of an implantable system according to the present disclosure.

With reference to FIG. 1*a*, in embodiments of the first aspect of the disclosure, the stimulation device 30 is configured to generate a plurality of different electrical signals for applying to the electrode pairs. This aspect of the disclosure may be practiced with at least two electrical signals, but a stimulation device according to the disclosure may be capable of generating any number different electrical signals. One electrical signal may differ from another if it differs by any one or more of the signal parameters described above, for example frequency, current amplitude, pulse duration.

In one embodiment, which is purely exemplary, the stimulation device is configured to generate three electrical signals.

The nerve stimulation system further comprises a control device 32 which causes the stimulation device 30 to deliver electrical signals to the electrode pairs. The control device has control logic that can control which of a plurality of electrical signals is delivered to which one(s) of the electrode pairs. For instance, in the case of each of arrays 1, 3 (each of which has 14 pairs of electrodes in the illustrated example, the pairs being named channels #1 to #14 for convenience) the control device may cause a first signal to be delivered to channel #3, a second signal to be delivered to channels #7 and #8 and a third signal to be delivered to channel #11. Of course, this is purely exemplary. Any combination of any number of signals may be delivered to any pair or pairs of electrodes, depending on the desired treatments that can be delivered through nerve bundles or fascicles in the complex nerve to which the system is attached. One signal may be delivered to one or more pairs, either adjacent or otherwise. Furthermore, one pair may deliver one or more signals (providing, of course, that those signals are not delivered simultaneously or else are multiplexed).

Purely by way of example, and with reference to FIG. 3*a*, a specific application of a nerve stimulation system according to the disclosure is shown. Here, a cross section of a cervical vagus nerve in the sheep is shown. Stimulating the vagus nerve with an 800 μA, 5 Hz signal can yield a number of different physiological responses, including cardiac effects, laryngeal effects and pulmonary effects. Through testing, nerve bundles or fascicles within the cervical vagus nerve were identified as being particularly effective for specific responses. For instance, fascicles within the cervical vagus nerve that were identified as being particularly effective for cardiac effects were found to be anatomically opposite (i.e. 180° from) fascicles also within the cervical vagus nerve that were identified as being particularly effective for pulmonary effects. Similarly, fascicles within the cervical vagus nerve that were identified as being particularly effective for laryngeal effects were found positioned between (i.e. 90° away from) both of the fascicles that were identified as being particularly effective for laryngeal effects and the fascicles that were identified as being particularly effective for pulmonary effects.

Accordingly, an embodiment of the disclosure suitable for treating cardiac, laryngeal and pulmonary effects in a sheep may include 14 electrode pairs (named channels #1 to #14 for convenience) evenly spaced around the circumference of the cuff, wherein the control device is configured to cause the stimulation device to deliver a first signal to channel #3 (the first signal suitable for treating cardiac effects), to deliver a second signal to channel #7 (the second signal suitable for treating laryngeal effects) and to deliver a third signal to channel #10 (the third signal suitable for treating pulmonary effects).

It will be noted that the fascicles identified as being particularly effective for impacting different physiologies are not uniform in size and/or number. Accordingly, it may be desirable to use greater or fewer channels to deliver a particular signal to particular nerve fascicles. For instance, in the example above, the second signal for treating laryngeal effects may be delivered to channels 6, 7 and 8 whilst the third signal for treating pulmonary effects may be delivered to channels 9, 10 and 11. Where signals are not delivered at the same time, it would be possible for one channel to be used for delivering two or more signals.

Figure 1B:
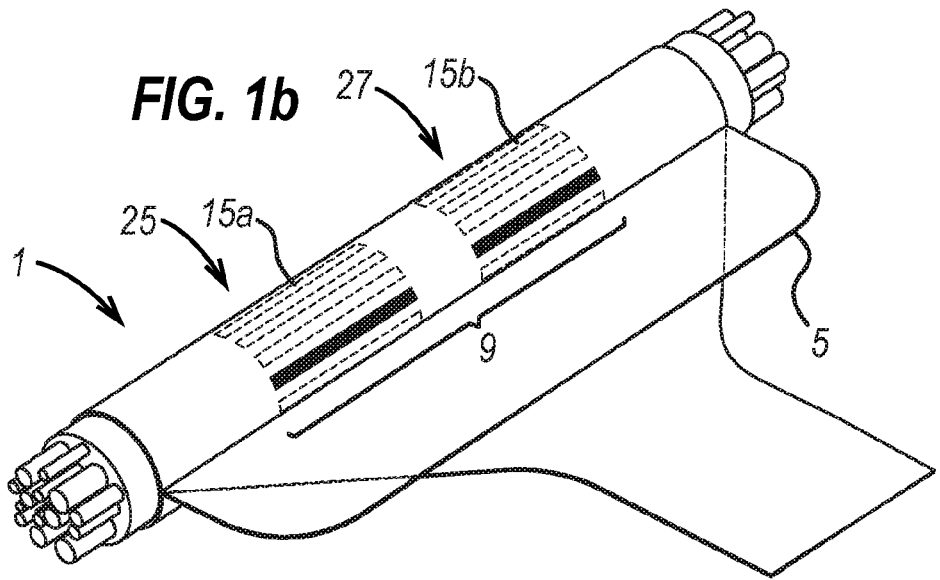
FIG. 1b illustrates a first embodiment of a nerve stimulation device for use with the present disclosure.
Figure 1C:
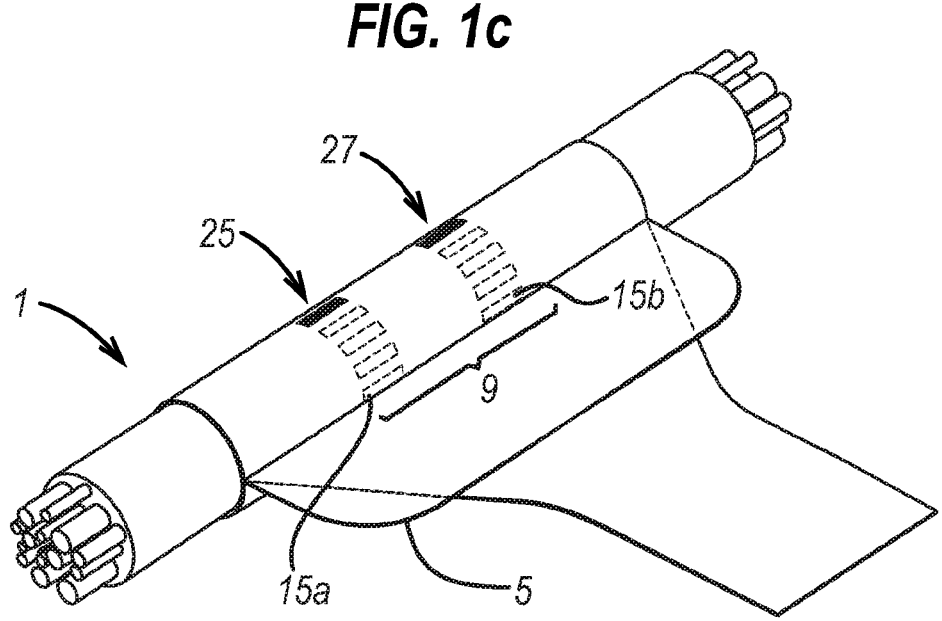
FIG. 1c illustrates a second embodiment of a nerve stimulation device for use with the present disclosure.
Figure 1D:
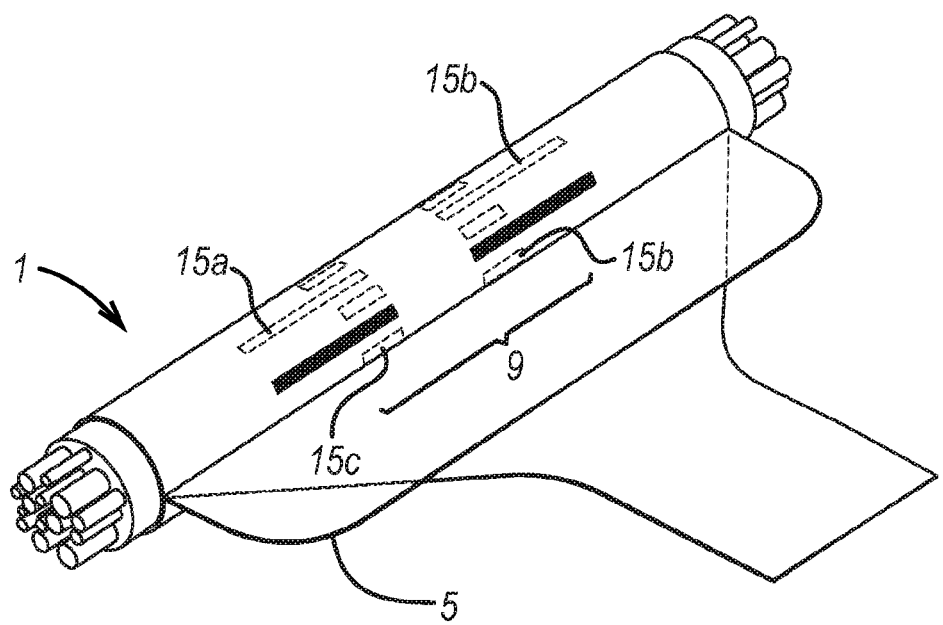
FIG. 1d illustrates a third embodiment of a nerve stimulation device for use with the present disclosure.

With reference to FIGS. 1*b* to 1*d* it will be noted that the electrode pairs may be configured in different ways to achieve improved selectivity in certain situations. As mentioned elsewhere herein, the array 1 shown in FIG. 1*b* comprises 14 pairs of circumferentially spaced-apart electrodes. More or fewer pairs of electrodes may be provided, but for certain nerves (e.g. the vagus nerve, which has a circumference of approximately 6 mm to 7 mm and is formed of nerve bundles or fascicles having an average diameter of 200 μm) 14 pairs is found to provide optimum selectivity. The electrodes 15*a*, 15*b*, 15*c*, 15*d* have identical geometries, and in particular a width of 0.2 mm and a length of 3 mm.

The array shown in FIG. 1*c* is identical to the array of FIG. 1*b*, except for the length of the electrodes, which are shorter. In particular, electrodes 15*a*, 15*b*, 15*c*, 15*d*, which all have identical geometries, have a width of 0.2 mm and a length of 1 mm.

As mentioned elsewhere herein the 1 mm long electrodes shown in the array of FIG. 1*c* mostly elicited fast fiber response (i.e. in myelinated fibers) whereas the 3 mm electrodes shown in the array of FIG. 1*b* stimulated both slow (i.e. unmyelinated) and fast fibers, but with a much higher proportion of slow fibers being stimulated. Geometries of the electrodes may also vary in terms of width, and shape.

The array shown in FIG. 1*d* is identical to the array of FIGS. 1*b* and 1*c*, except that the electrodes 15*a*, 15*b*, 15*c*, 15*d* do not all have identical geometries. As shown, electrodes 15*a*, 15*b* belong to a first subset of electrode pairs having a first geometry and electrodes 15*c*, 15*d* belong to a second subset of electrode pairs having a second geometry different from the first. In particular, the lengths of the electrodes in the pairs belonging to the first subset is different from the lengths of the electrodes in the pairs belonging to the second subset. Specifically, the electrodes 15*a*, 15*b* have a width of 0.2 mm and a length of 1 mm (for stimulating fast fibers), whereas electrodes 15*c*, 15*d* have a width of 0.2 mm and a length of 3 mm (for stimulating slow fibers). Again, these geometries are purely exemplary and may be of different magnitudes. Geometries of the electrodes may also vary in terms of width, and shape.

In the array shown in FIG. 1*d*, both electrodes in each electrode pair have the same geometry, but again this need not be the case and the geometries, in particular the lengths, of the electrodes in each pair may differ.

In the array shown in FIG. 1*d*, the first and second subsets are arranged in an alternating pattern such that either side of each electrode pair in the first subset is an electrode pair in the second subset and vice versa. This is to enable optimal selective stimulation of fast and slow fibers distributed evenly around the nerve. However, this need not be the case and the subsets may be arranged in whatever pattern is appropriate. For example, the first subset may exclusively occupy a first arc of the circumference and the second subset may exclusively occupy a second arc of the circumference. This would enable optimal selective stimulation of fast and slow fibers that are gathered together in certain regions of the nerve.

In embodiments of the second aspect of the disclosure, the stimulation device 30 is configured to generate one or more electrical signals for applying to the electrode pairs. This aspect of the disclosure may be practiced with at least one, electrical signal, though two or more are used in some embodiments and a stimulation device according to the disclosure may be capable of generating any number different electrical signals.

The control device 32 of these embodiments again causes the stimulation device to deliver electrical signal(s) to the electrode pairs. The control device has control logic that can control which electrical signal(s) is/are delivered to which one(s) of the subset of the electrode pairs. For instance, the control device may be configured to deliver a signal to the electrode pairs of the first subset but not the second subset, or vice versa. Alternatively, the control device may be configured to deliver a first signal to one or more or all of the electrode pairs of the first subset and to deliver a second signal to one or more or all of the electrode pairs of the second subset. Of course, this is purely exemplary. Any combination of any number of signals may be delivered to any pair or pairs of electrodes, depending on the desired treatments that can be delivered through nerve bundles or fascicles in the complex nerve to which the system is attached.

The control system of the first and/or second aspects of the system may be further configured to deliver one or more or all signal(s) to the electrode pairs either according to a schedule or upon receipt of a trigger. The schedule may be configured by a physician and stored in a memory of the system, and may be reconfigured as required. The trigger may be a user-initiated trigger or an automated trigger based on the detection of physiological activity.

The system may also comprise a physiological sensor arranged to detect physiological activity in a subject. This sensor may be used to detect activity in the subject such as heart rate or EMG activity in a muscle.

In one example application, the control system may be configured to deliver a first signal every 20 minutes. Of course, this time period is only exemplary and shorter or longer time periods are possible depending on application and including every 20 minutes, 30 minutes, 1 hour, 2 hours, 3 hours, 4 hours, 6 hours, 12 hours, 24 hours, 48 hours, 72 hours, week and month. The control system may be configured to deliver a second signal according to the same or a different schedule. Where the schedule is the same, it may be offset in time such that the delivery of the first and second signals is not taking place simultaneously.

In another example application, the control system may be configured to deliver a first signal upon receipt of a first trigger, wherein the trigger is user-initiated. For example, the first signal may be suitable for treating a disease whose symptoms are perceptible by a user such as anxiety or pain. A user device such as a portable interface (not shown), or a smartphone or watch loaded with software configured to communicate with the nerve stimulation system may be used to generate the user-initiated trigger by pressing a button. The control system may be configured to deliver a second signal upon receipt of a second trigger, wherein the trigger is generated by (or the result of data from) a physiological sensor arranged to detect physiological activity in a subject. For example, a physiological sensor may be configured to detect heart rate and a trigger activated when heart rate increases beyond a threshold, for example.

It will be appreciated that any combination of schedules and triggers may be used, depending on circumstances.

In one example application, the electrodes of the arrays are placed on the right vagus nerve of anesthetized adult sheep and stimulation is applied between electrode pairs. In this example, the arrays are arranged in a similar fashion to that illustrated in FIG. 1 with the nerve 13 being the vagus nerve of the sheep.

Figure 3B:
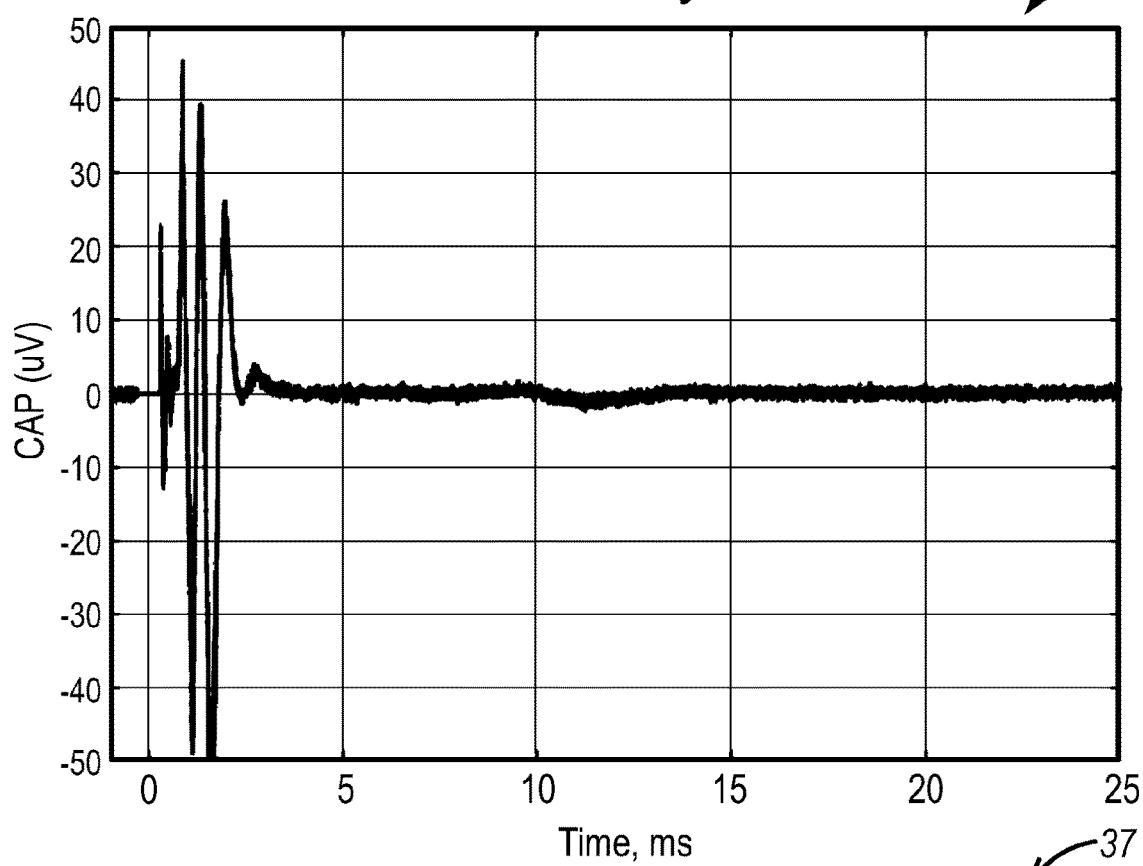
Figure 3B:
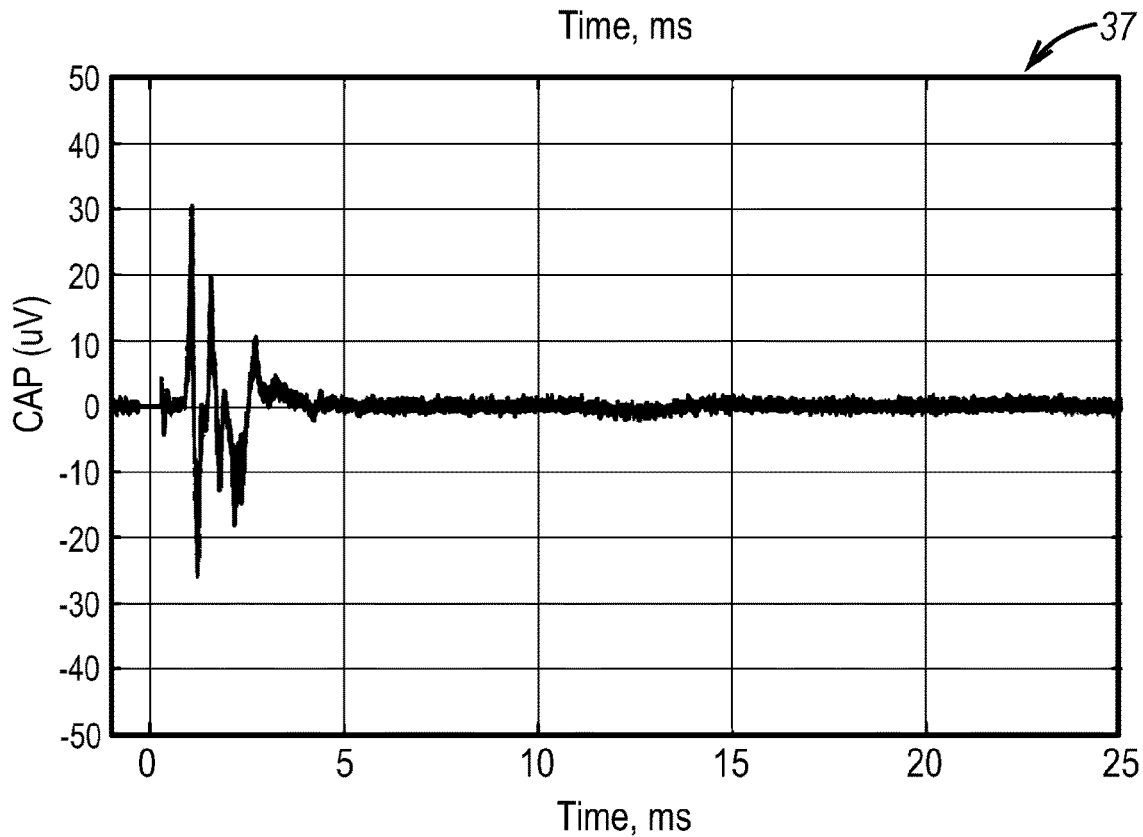

FIG. 3b illustrates a number of charts which show the response induced in the nerve 13 when stimulation was applied to the electrode pairs. Charts 35 and 37 illustrate the compound action potential (CAP) measured in the nerve of different sheep when stimulation was applied to electrode pairs of the second array 2. On the other hand, charts 39 and 41 illustrate the CAP measured in the nerve of different sheep when stimulation was applied to electrode pairs of the second array 2. Referring to FIG. 3b, the peak appearing at around 10 ms of delay in the nerve recording represents an EMG contamination from the contraction of the trachea and larynx, pronounced in the 3 mm electrode.

It was found that in any of the electrode pairs of the second array 3, the 1 mm long electrodes mostly elicited fast fiber response (myelinated fibers). In addition, it was found that the longer electrode arrays of the first array 1 stimulated both slow (unmyelinated) and fast fibers, but with a much higher proportion of slow fibers (unmyelinated) being stimulated. This was found when either the same current or the same charge density were applied in either one of the electrode arrays.

Furthermore, it was found that the first array 1 was able to reliably cause bradypnea (slow breathing) when stimulating the vagus nerve. On the other hand, the second array 2 always failed to achieve this (with any of the tested combination of electrodes) even at much higher charge densities.

Figure 4:
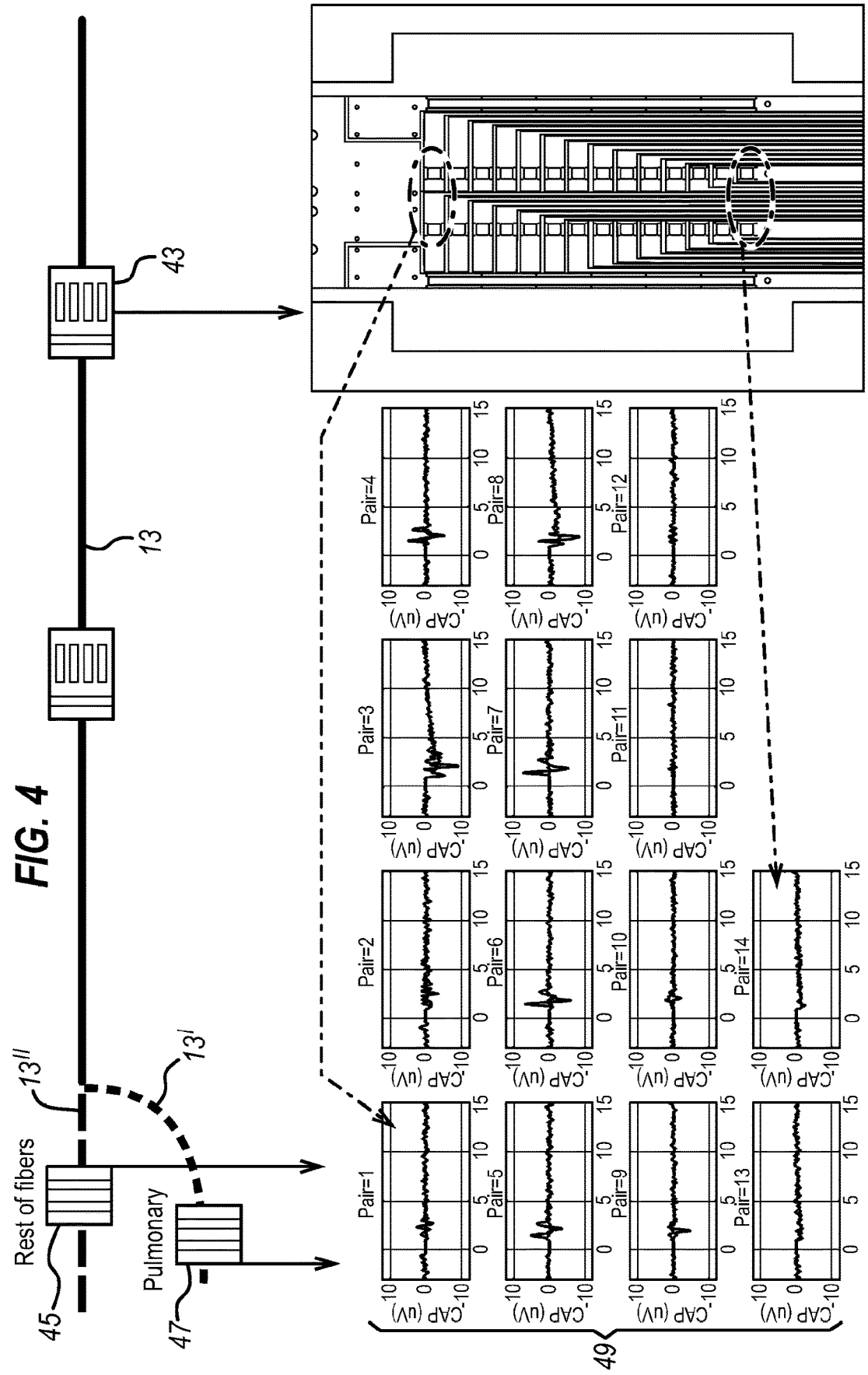
FIG. 4 illustrates further measurements of CAP measured in response to stimulation of a nerve using the nerve stimulation devices.

The arrays described above have been shown to selectively stimulate specific nerve fibers in a nerve. Referring to FIG. 4, arrays comprising two electrode rings each comprising 14 electrodes were used to selectively stimulate nerve fibers. Here, each electrode had a surface of 0.2 mm in width and 0.2 mm in length, and each pair of electrodes were 1 mm apart. One such array 43, was positioned on the vagus nerve 13 of a subject in order to provide selective stimulation to the nerve.

A stimulation device was used to generate electrical signals. In this example, the signals comprise bipolar stimulating pulses with a current of 500 µA, a pulse width of 0.1 ms and a frequency of 5 Hz. These signals were applied to electrode pairs, one longitudinal pair at a time. CAP responses to the stimulation were measured using an array 47 placed on the pulmonary branch 13' of the nerve 13 and another array 45 placed on the rest of descending vagus nerve fibers 13". For example, a CorTec array may be used.

The activation patterns for each of the 14 pairs of electrodes are illustrated in the chart 49. In the charts 49 the lines represent the readings from the pulmonary branch and the readings from the rest of vagus nerve fibers.

As illustrated, it can be seen that there was a significant difference in the activation patterns depending on the pairs of electrodes being stimulated at a particular time. Therefore, it will be appreciated that the electrode array 43 is capable of selectively stimulating nerve fibers in a nerve.

In one example, in order to optimize electrode configuration for optimal differential activation of fascicles within a target nerve, which is the vagus nerve in this example, an in-silico model was initially used. A 3D cylindrical model of the human-sized vagus nerve was produced in the COMSOL simulation software. The model was 2.8 mm in diameter, and had 2 compartments: intraneural space with fascicles (effective average conductivity 0.3 S/m), and 100 µm-thick epineurium (0.083 S/m, (Calvetti et al., 2011)) surrounding the latter (FIG. 4A(i)). The discretization was performed according to mesh convergence criteria with the smallest electrode sizes, resulting in the optimal mesh to be 5M regular tetrahedral elements refined in the area of electrode application. The electrodes were placed via applying a complete electrode model on the elements occupying relevant areas of the outer surface of the model in order to simulate effects of the current redistribution due to a contact impedance (Somersalo et al., 1992). Two radially located "virtual fascicles" were placed beneath the electrodes, one ⅓ and another ⅔ of the radius deep (see FIG. 4B), to serve as a target for neuronal stimulation. Threshold current density for fascicle activation is based on historical literature (Warman et al., 1992).

Figure 4A:
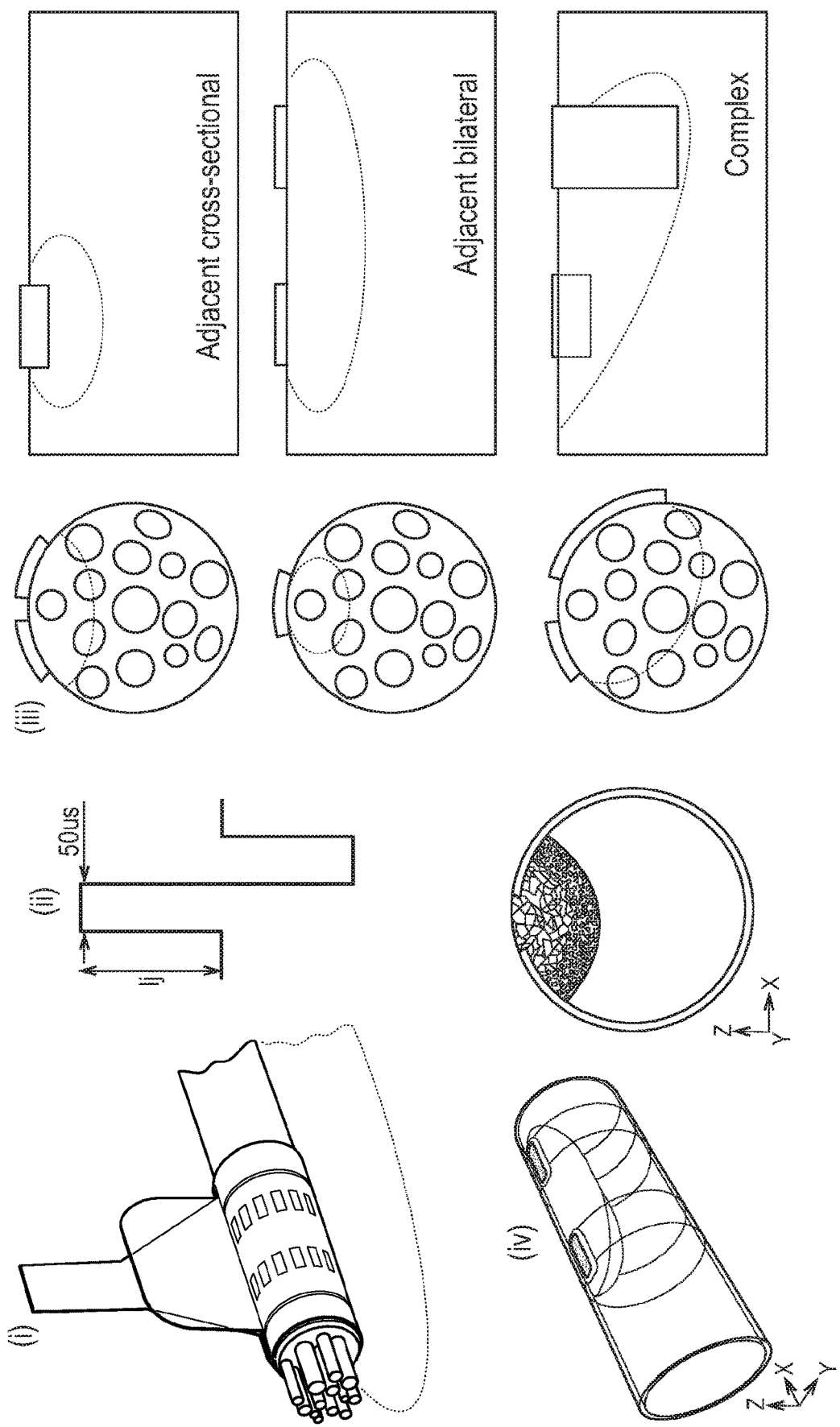
FIG. 4A illustrates examples of modelled stimulations.

FIG. 4A illustrates examples of modelled stimulations. In FIG. 4A(i) there is an image which illustrates the 3D rendering of the human-sized vagus nerve with a cuff electrode around the nerve; FIG. 4A(ii) is an image which illustrates the representative pulse used for simulations as well as for in vivo experiments. The pulse width per phase in this example experiment was 50 µs; FIG. 4A(iii) is a schematic representation of the cross section of the vagus nerve and includes indications of different electrode arrangements used during optimization model. The boxes on the right represent the arrangement of the electrode along the longitudinal axis of the nerve; and FIG. 4A(iv) illustrates two images which show the activation area in the nerve, represented longitudinally and in cross-section, during a simulated stimulation with adjacent bilateral electrodes.

FIG. 4B illustrates modelling results. The graphs summarize the modelling results, and the optimized electrode designed obtained by modelling recruitment of superficial and deep fascicles.

The simulations were performed for each sets of parameters ($p_i$): Electrode Width: 0.05-2.0 mm, Electrode Length 0.5-4.5 mm, and Distance between electrodes: 0.5-4.5 mm, evaluating the minimum current which is required to activate the fascicle, and computing total current distribution given this criterion. Then total activated area in the cross-section (above the activation threshold) $A(J>J_a)$ and maximum current density directly beneath the electrodes ($J_m$) were calculated. Before considering the complex geometrical arrangements, the symmetrical longitudinal bipolar configuration was optimized by varying electrode width, length, and distance between the electrodes.

The model shows that a bipolar configuration produces an absolute minimum on objective function over all possible extended geometrical arrangements, and hence completes the optimization process. The model also shows that the ideal electrode design consisted of an electrode width of 0.35 mm, length of 3.0 mm and interelectrode distance (between 1 electrode in 1 ring and the paired electrode on the second ring) of 3.0 mm and 14 pairs of electrodes (14 for each ring). Selected optimal parameters were then slightly adjusted (width of electrode was 0.2 mm, with 0.2 mm distance between two consecutive electrodes) given the practicality of the manufacturing and in-vivo experimental requirements, and optimal designs were produced.

Referring again to FIG. 1, another example of selective stimulation will be described. In this example, an in-vivo experiment was conducted in which selective stimulation was combined with electrical impedance tomography (EIT) imaging. Two arrays 1, 3 were implanted on the right cervical vagus nerve 13 of an anesthetized sheep. The first array 1 (Array A) was used to stimulate the nerve 13, whilst the second array 3 (Array B) was used for CAP recording and EIT imaging. The arrays 1, 3 were placed 40 mm apart. In addition, physiological sensors were used to measure physiological parameters, such as end tidal CO2 (EtCO2), electrocardiogram (ECG), blood pressure (BP), heart rate (HR), respiration rate (RR) and peripheral capillary oxygen saturation (SpO2) in the subject. The specific electrode arrays described above with reference to FIG. 2 were used in this example. Although, EIT imaging has been used as an example herein, it is envisaged that other techniques could be used, such as electroneurogram (ENG) recording.

Figure 5:
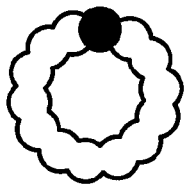
FIG. 5 illustrates the position of electrode pairs in the nerve stimulation devices.
Figure 5:
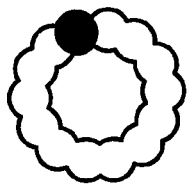
Figure 5:
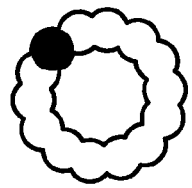
Figure 5:
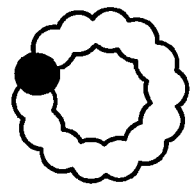
Figure 5:
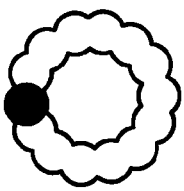
Figure 5:
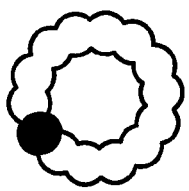
Figure 5:
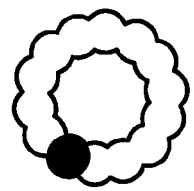
Figure 5:
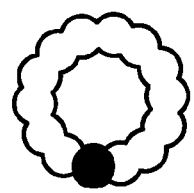
Figure 5:
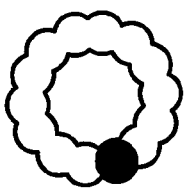
Figure 5:
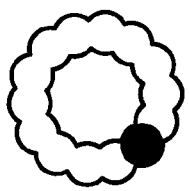
Figure 5:
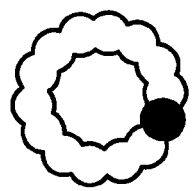
Figure 5:
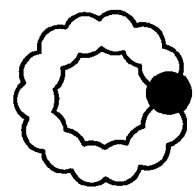
Figure 5:
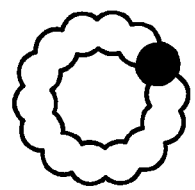
Figure 5:
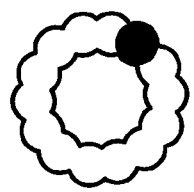

One longitudinal pair at a time was stimulated with 20 Hz frequency, 0.05 ms pulse width, biphasic stimulation pulses, in total lasting 60 seconds. This was followed by rest period lasting another 60 seconds. Then, the adjacent pair of electrodes in the array was selected and the protocol repeated for all of the electrodes. The position of each of the electrode pairs is illustrated schematically in FIG. 5, in which the solid circle represents the position of the electrode pair relative to the other pairs.

Figure 6A:
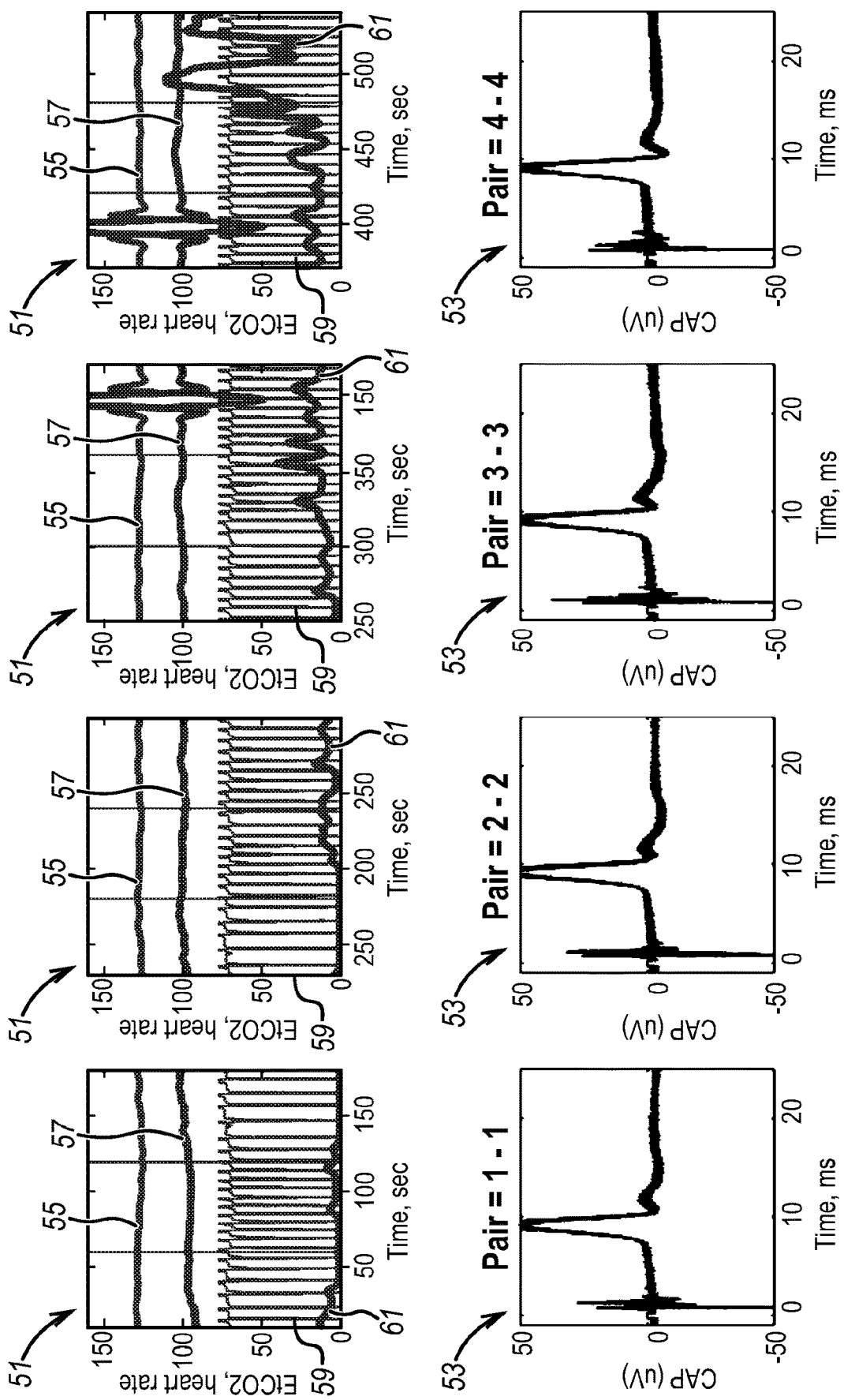
FIGS. 6A and 6B illustrate measurements of physiological activity and CAP measured in response to stimulation of a nerve using the nerve stimulation devices.
Figure 6B:
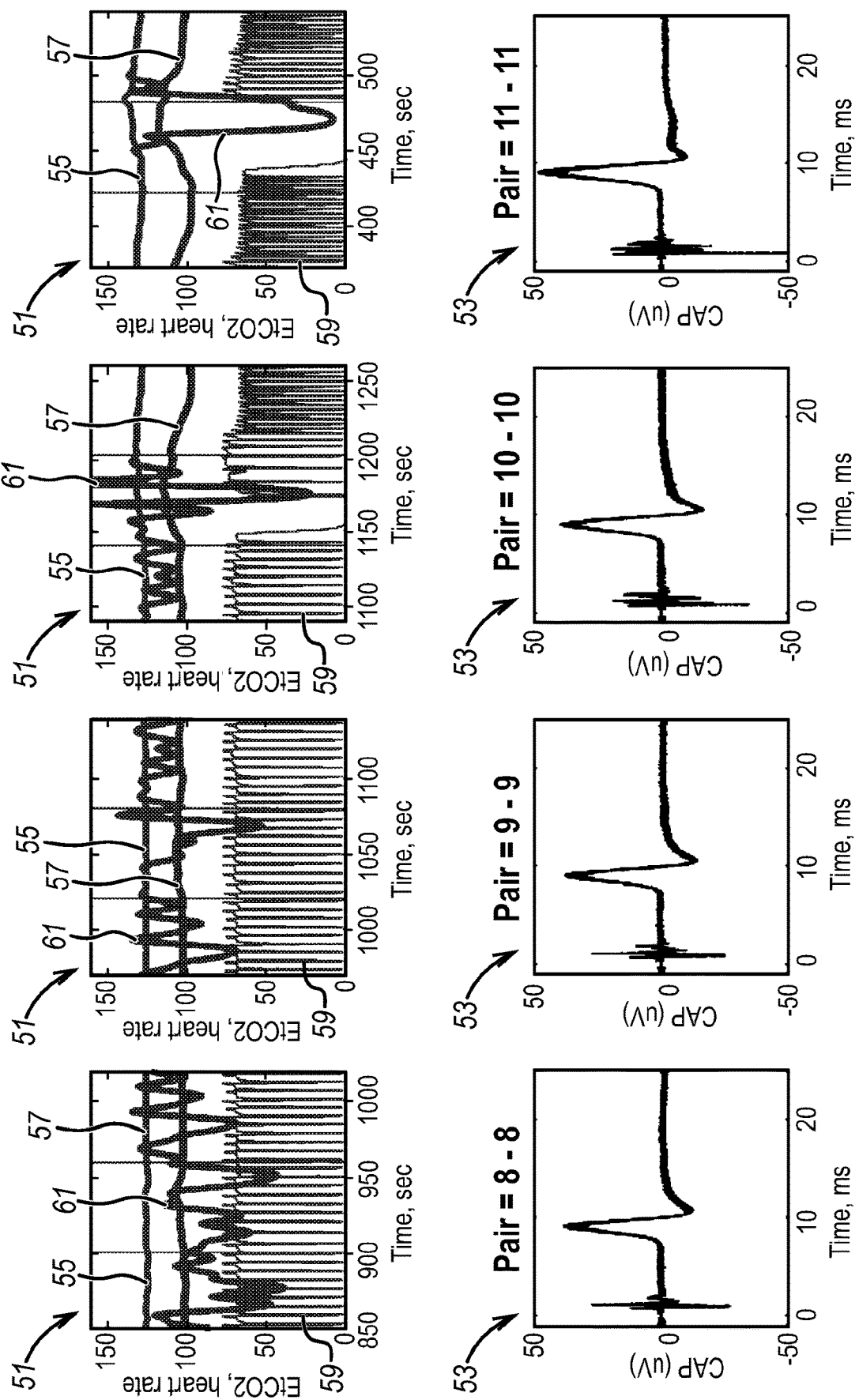

The process of stimulating the electrode pairs lasted 28 minutes during which RR, BP, EtCO2, SpO2 and ECG were constantly monitored. The results of this process are illustrated in FIG. 6A and FIG. 6B in which the upper chart 51 for each pair shows physiological data and the lower chart 53 for each pair shows the average CAP measured during 60 s of stimulation. Referring to FIG. 6A and FIG. 6B, the peak appearing at around 10 ms of delay in the nerve recording represents an EMG contamination from the contraction of the trachea and larynx.

In the upper charts 51 showing physiological data the line 55 shows HR, the line 57 shows BP and the dark line 59 shows EtCO2 indicative of breathing pattern. The line 61 shows HR measured from ECG; however, the HR from ECG readings tended to be inconsistent and, thus, will be ignored for the purposes of this example.

As illustrated in the charts 51, stimulation of specific pairs of electrodes can induce specific physiological responses. For example, stimulation of pairs 3 and 4 resulted in a change in HR and blood pressure. As another example, stimulation of pairs 10-12 resulted in a changed in breathing pattern. In this way, it is possible to determine that specific nerve fibers in proximity to the electrodes of a particular pair are associated with specific organs and physiological responses.

After selective stimulation process, a first pair of electrodes which provided the most prominent pulmonary response was selected. Then, another 3 pairs were selected: the pair opposite the first pair, the pair located 90o clockwise of the first pair and the pair located 90o anti-clockwise of the first pair. This resulted in the selection of 4 pairs, each located at 4 equidistant points around the circumference of the array. Then, by stimulating 1 pair at a time, full EIT recording was performed using the opposite array. In this example, a 14-pair injecting protocol was used with 30 seconds per injection for EIT recording. This required 7 mins per imaging data set. The EIT signal used has a frequency of 6 kHz and 9 kHz, with a current amplitude of 100 uA. Thus, when EIT was combined with stimulation of the most respiratory effective pair of electrodes and the opposing pair, different areas for the vagus nerve were imaged. The results of the EIT imaging process are illustrated in FIG. 7.

Figure 7:
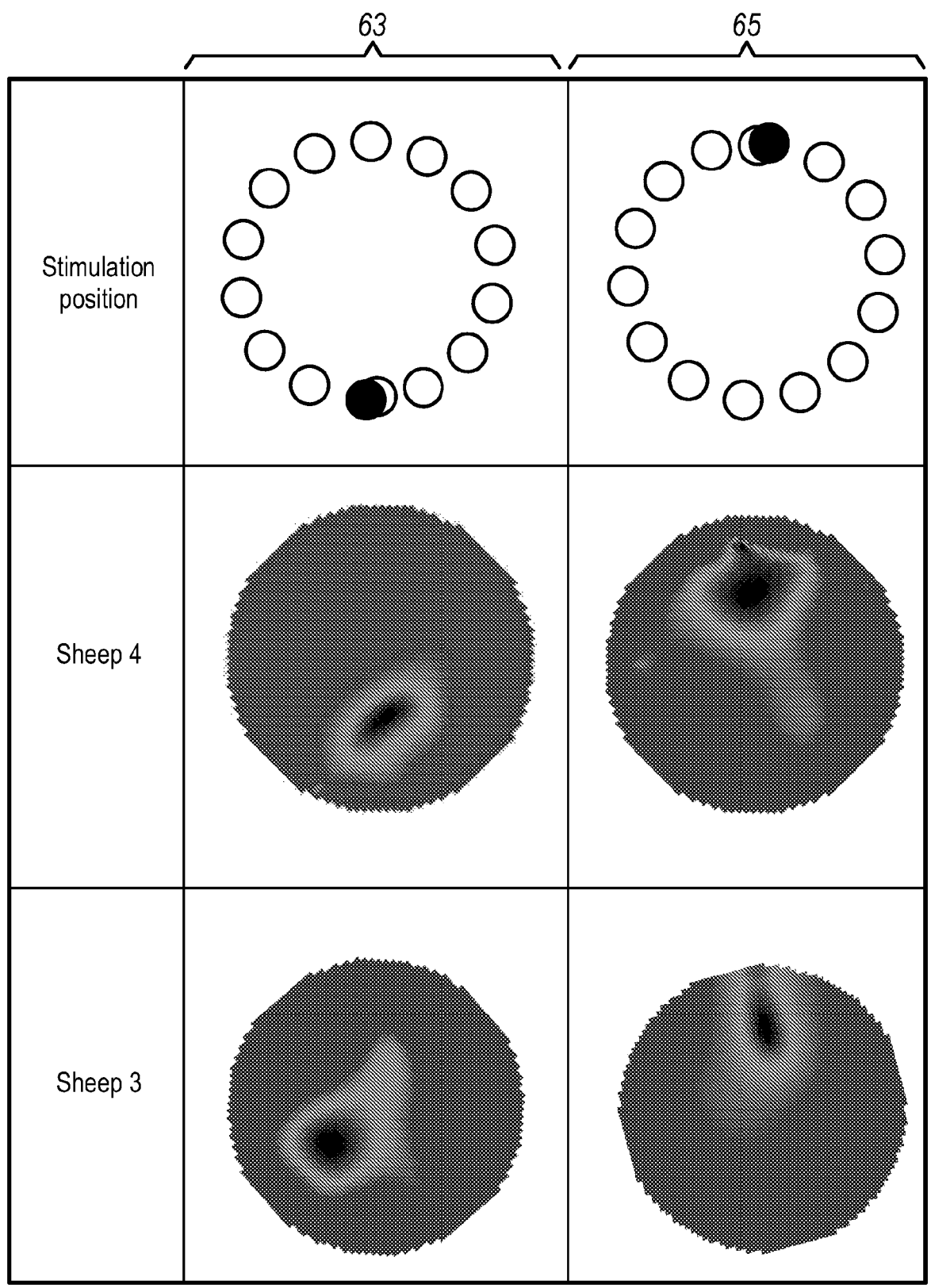
FIG. 7 illustrates images of nerve activity.

Referring to FIG. 7, the images show EIT imaging reconstruction obtained in two different sheep when selective stimulation was performed with array B, and EIT recording was performed with array A. The images in the first column 63 show the EIT images obtained during stimulation of an electrode pair that was found not to cause any respiratory change. The images in the second column 65 show the EIT images obtained during stimulation of an electrode pair that was found to cause respiratory changes. Therefore, it has been shown that the electrode arrays described herein allow specific nerve fibers to be selectively stimulated and imaged. Again, although, EIT imaging has been used as an example herein, it is envisaged that other techniques could be used, such as electroneurogram (ENG) recording.

Figure 7A:
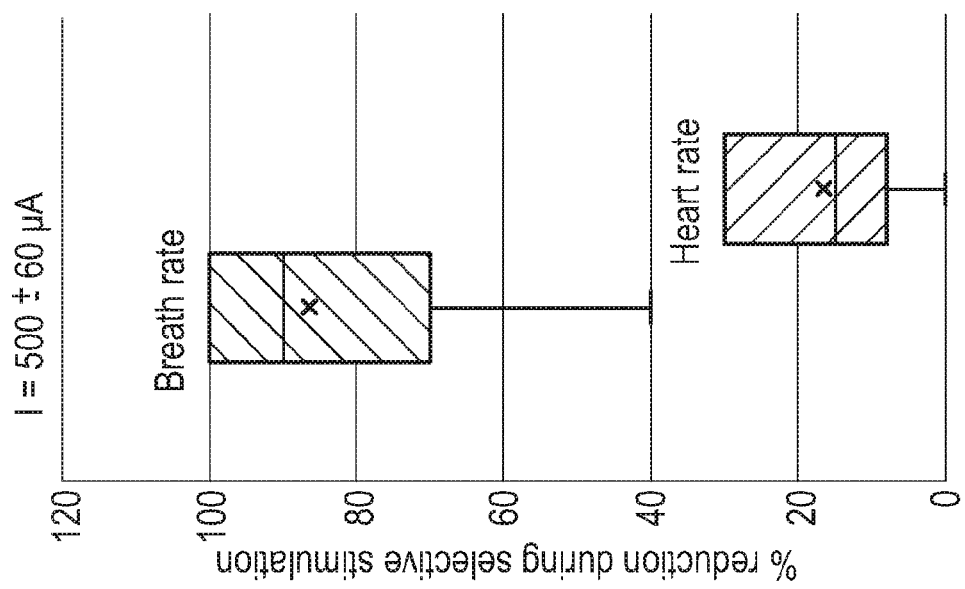
FIG. 7A illustrates in vivo data obtained using an optimized design.
Figure 7A:
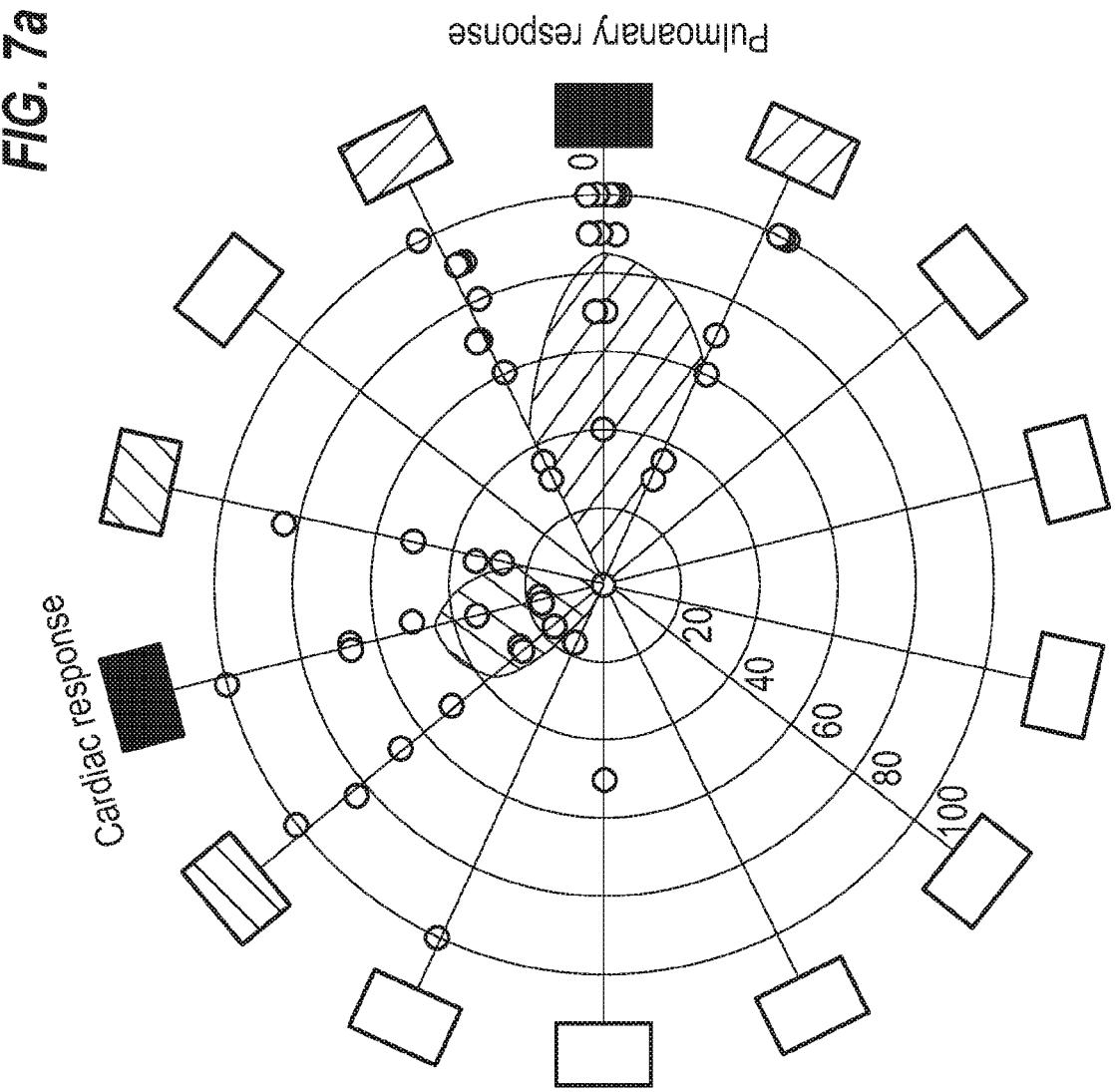

The in vivo data obtained using the optimized optimised design are summarized in FIG. 7A. Stimulation of the right cervical vagus nerve, in anesthetized sheep (N.8), using a 15 electrode pair cuff electrode, selectively induced cardiovascular responses (defined as bradycardia and hypotension, vs. baseline values) and pulmonary responses (defined as an increase in the expiratory time and decrease in respiratory rate, vs. baseline values). The relative fascicle positions and the magnitude of the observed physiological effect is shown in FIG. 7A.

FIG. 7A illustrates the estimated location of cardiovascular and pulmonary fascicles in the vagus nerve based on cardiovascular and pulmonary effects cause by stimulation. The average magnitude (N=8)±s.d. of the responses are shown in the graph on the right.

In another example, an implantable system for stimulating and/or monitoring activity in a nerve is provided. This system includes at least one nerve interface device, which may correspond with one or more of the nerve interface device described above. The at least one nerve interface device is arranged, in use, to apply an electrical signal to at least one nerve fiber of a subject. The electrical signal may be applied in a manner consistent with that described above.

The implantable system may comprise a signal generator which is configured to generate a signal to be delivered to the at least one nerve fiber by the first pair of electrodes of the nerve interface device to modulate neural activity within the at least one nerve fiber. The implantable system may also comprise a control sub-system configured to cause the signal generator to deliver the signal to the first pair of electrodes.

The control sub-system may be configured to cause the signal generator to deliver the signal to the first pair of electrodes upon receiving a trigger generated by an operator. In addition, or as an alternative, the control sub-system may be configured to cause the signal generator to deliver the signal to the first pair of electrodes according to a predetermined pattern.

The implantable system may further comprises a detection sub-system configured to detect activity within the at least one nerve fiber at the first pair of electrodes. In this way, the system is able to monitor activity in the nerve, for instance, via imaging the nerve using a technique such as EIT imaging or ENG recording.

The implantable system may be further configured to generate probe electrical signals to be delivered to the at least one nerve fiber by the first pair of electrodes to cause a corresponding electrical response within the at least one nerve fiber. The system may further comprise: a stimulation sub-system configured to cause the signal generator to deliver the probe electrical signals to the first pair of electrodes. The detection sub-system may be configured to detect an electrical response within the at least one nerve fiber at the first pair of electrodes.

The implantable system may further comprise one or more physiological sensors configured to detect physiological activity that is associated with corresponding neural activity within the at least one nerve fiber. An example of a physiological sensor is an ECG monitor, which can be used to monitor heart activity. In one example, the neural activity is autonomic neural activity. In particular, the detection sub-system is configured to detect the corresponding neural activity within the at least one nerve fiber at the first pair of electrodes.

The implantable system discussed herein may comprise at least one nerve interface device. Examples of nerve interface devices are described above. The stimulation sub-system may be configured to generate probe electrical signals to be delivered to the at least one nerve fiber by each of the plurality of pairs of electrodes of the nerve interface device.

The implantable system may comprise processing means configured to determine, based on the electrical responses and/or corresponding neural activity detected by the detection subsystem, electrical properties at one or more locations within the nerve fiber.

The control sub-system may be configured to determine one or more pairs of electrodes for delivering the signal based on the one or more locations within the nerve fiber at which the detection subsystem determined the electrical properties.

There is also provided a method of modulating activity in at least one nerve fiber of a subject which uses the system described herein. In the method, the system causes the signal generator to deliver a signal to the first pair of electrodes. Then, the signal is delivered via the first pair of electrodes to the at least one nerve fiber. In one example, the signal generator may be initiated to deliver the signal upon receipt of a trigger signal generated by an operator. In another example, the signal generator may be initiated to deliver the signal according to a predetermined pattern.

The method may further comprise detecting, via the first pair of electrodes, activity in the nerve. The method may further comprise delivering a probe electrical signal to the nerve via the first pair of electrodes, wherein the activity in the nerve that is detected via the first pair of electrodes is an electrical response caused by the probe electrical signal. The activity in the nerve that is detected via the first pair of electrodes may be neural activity caused by corresponding physiological activity.

In another example, there is an implantable system for stimulating and monitoring activity in a nerve. This system may comprise first and second nerve interface devices, which may be any one the devices described above. The first device may be arranged, in use, to apply an electrical signal to at least one nerve fiber of a subject. In addition, the second device may be arranged, in use, to detect said electrical signal in the at least one nerve fiber.

The system may further comprise a signal generator configured to generate a signal to be delivered to the at least one nerve fiber by the first pair of electrodes in the first nerve interface device to modulate neural activity within the at least one nerve fiber; a control sub-system configured to cause the signal generator to deliver the signal to the first pair of electrodes in the first nerve interface device; and a detection sub-system configured to detect activity within the at least one nerve fiber at the first pair of electrodes in the second nerve interface device.

In another example, there is a method of stimulating and monitoring activity in at least one nerve fiber of a subject. The method may use an implantable system, which may be one of the systems described above. The method may comprise the steps of causing the signal generator to deliver a signal to the first pair of electrodes in the first nerve interface device; and detecting via the first pair of electrodes in the second nerve interface device activity in the nerve, the activity caused by the signal delivered to the at least one nerve fiber by the first pair of electrodes in the first nerve interface device.

An Implantable Device/System for Implementing Embodiments of the Disclosure

Figure 8:
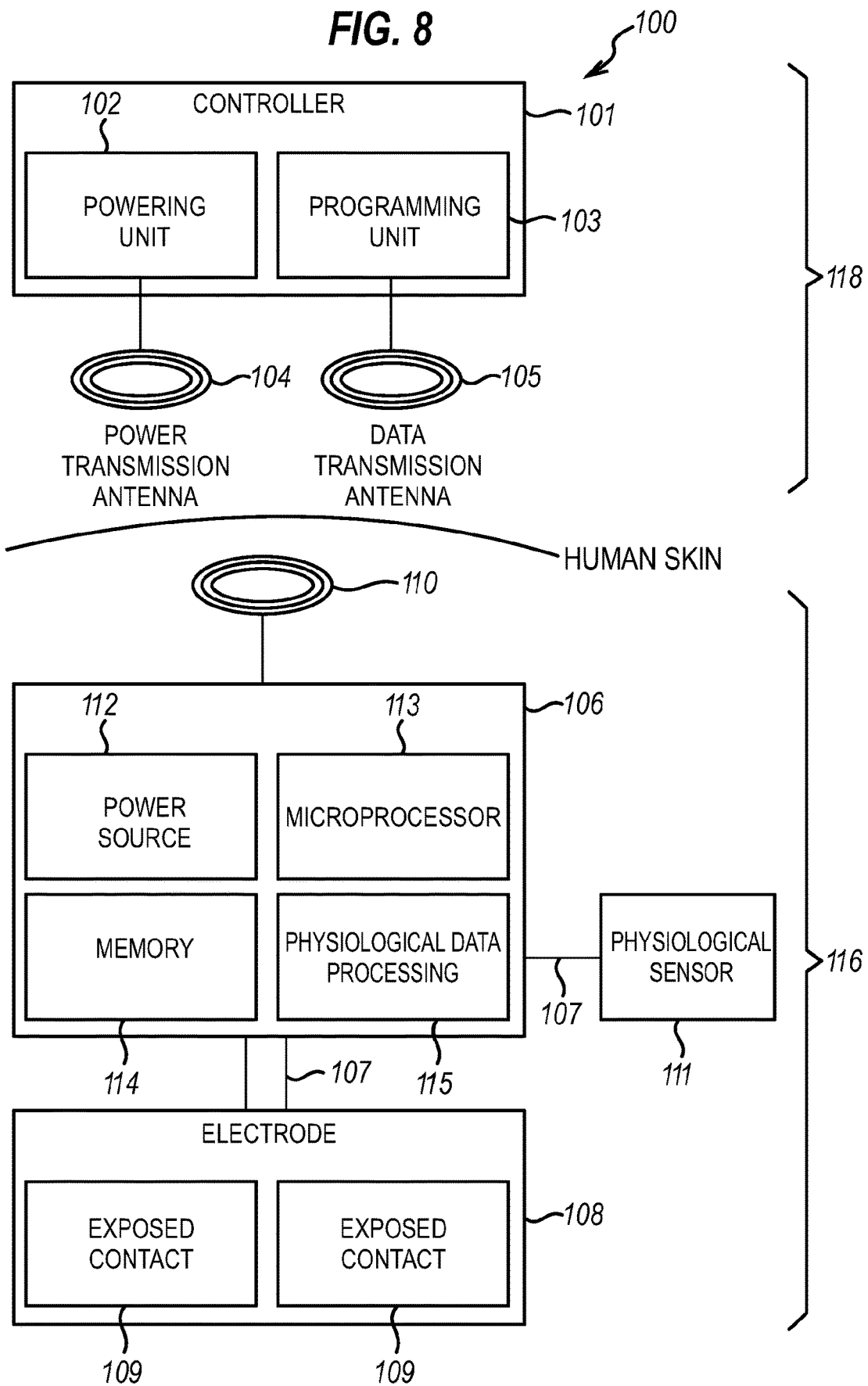
FIG. 8 illustrates an overview of the system.

An implantable system according to the disclosure comprises an implantable device (e.g. implantable device 106 of FIG. 8). The implantable device comprises at least one neural interfacing element such as a transducer, for example an electrode (e.g. electrode 108), suitable for placement on, in, or around a nerve. As will be appreciated, the implantable system also provides a stimulation device such as a current or voltage source, and a power source such as a battery. The implantable system also can comprise a processor (e.g. microprocessor 113) coupled to the at least one neural interfacing element.

The at least one neural interfacing element may take many forms, and includes any component which, when used in an implantable device or system for implementing the disclosure, is capable of applying a stimulus or other signal that modulates electrical activity in a nerve.

The various components of the implantable system can be part of a single physical device, either sharing a common housing or being a physically separated collection of interconnected components connected by electrical leads (e.g. leads 107). As an alternative, however, the disclosure may use a system in which the components are physically separate, and communicate wirelessly. Thus, for instance, the at least one neural interfacing element (e.g. electrode 108) and the implantable device (e.g. implantable device 106) can be part of a unitary device, or together may form an implantable system (e.g. implantable system 116). In both cases, further components may also be present to form a larger device or system (e.g. system 100).

Suitable Forms of a Modulating Signal

Embodiments of the disclosure use a signal applied via one or more neural interfacing elements (e.g. electrode 108) placed in signaling contact with a nerve.

Signals applied according to the disclosure are ideally non-destructive. As used herein, a "non-destructive signal" is a signal that, when applied, does not irreversibly damage the underlying neural signal conduction ability of the nerve. That is, application of a non-destructive signal maintains the ability of the nerve (e.g. a nerve) or fibers thereof, or other nerve tissue to which the signal is applied, to conduct action potentials when application of the signal ceases, even if that conduction is in practice artificially stimulated as a result of application of the non-destructive signal.

The signal will usually be an electrical signal, which may be, for example, a voltage or current waveform. The at least one neural interfacing element (e.g. electrode 108) of the implantable system (e.g. implantable system 116) is configured to apply the electrical signals to a nerve, or a part thereof. However, electrical signals are just one way of implementing the disclosure, as is further discussed below.

An electrical signal can take various forms, for example, a voltage or current. In certain such embodiments the signal applied comprises a direct current (DC) or an alternating current (AC) waveform, or both a DC and an AC waveform. A combination of DC and AC is particularly useful, with the DC being applied for a short initial period after which only AC is used. As used herein, "charge-balanced" in relation to a DC current is taken to mean that the positive or negative charge introduced into any system (e.g. a nerve) as a result of a DC current being applied is balanced by the introduction of the opposite charge in order to achieve overall (net) neutrality. In other words, a charge-balance alternating current includes a cathodic pulse and an anodic pulse.

In certain embodiments, the AC waveform may be a square, sinusoidal, triangular, trapezoidal, quasitrapezodial or complex waveform. The DC waveform may alternatively be a constant amplitude waveform. In certain embodiments the electrical signal is an AC sinusoidal waveform. In other embodiments, waveform comprise one or more pulse trains, each comprising a plurality of charge-balanced biphasic pulses.

The signal may be applied in bursts. The range of burst durations may be from sub-seconds to minutes, and in rare occasions, hours; applied continuously in a duty cycled manner from 0.01% to 100%, with a predetermined time interval between bursts. The electric signal may be applied as step change or as a ramp change in current or intensity. Particular signal parameters for modulating (e.g. stimulating) a nerve are further described below. In one example, the duty cycle of a signal intermittently stimulating a nerve is based on the type of disease or physiology that is being targeted. In addition, indicative feedback may be provided by measuring physiological changes caused due to the stimulation provided and/or clinician input may be provided to update the duty cycle of the signal.

Modulation of the neural activity of the nerve can be achieved using electrical signals which serve to replicate or magnify the normal neural activity of the nerve.

Signal Parameters for Modulating Neural Activity

In all of the above examples, a signal generator may be configured to deliver an electrical signal for modulating (e.g. stimulating) a nerve (e.g. the vagus nerve). In the present application, the signal generator is configured to apply an electrical signal with certain signal parameters to modulate (e.g. stimulate) neural activity in a nerve (e.g. the vagus nerve). Signal parameters for modulating (e.g. stimulating) the nerve, which are described herein, may include waveform shape, charge amplitude, pulse width, frequency, and duration.

It will be appreciated by the skilled person that the current amplitude of an applied electrical signal necessary to achieve the intended modulation of the neural activity will depend upon the positioning of the electrode and the associated electrophysiological characteristics (e.g. impedance). It is within the ability of the skilled person to determine the appropriate current amplitude for achieving the intended modulation of the neural activity in a given subject.

Electrodes

As mentioned above, the implantable system comprises at least one neural interfacing element, the neural interfacing element can be an electrode 108. The neural interface is configured to at least partially and in some embodiments fully circumvent the nerve. The geometry of the neural interface is defined in part by the anatomy of the nerve.

In some embodiments (for example, FIG. 8), electrode 108 may be coupled to implantable device 106 of implantable system 116 via electrical leads 107. Alternatively, implantable device 106 may be directly integrated with the electrode 108 without leads. In any case, implantable device 106 may comprise AC or DC output circuits, optionally based on capacitors and/or inductors, on all output channels (e.g. outputs to the electrode 108, or physiological sensor 111). Electrode 108 may be shaped as one of: a rectangle, an oval, an ellipsoid, a rod, a straight wire, a curved wire, a helically wound wire, a barb, a hook, or a cuff. In addition to electrode 108 which, in use, is located on, in, or near a nerve (e.g. the vagus nerve), there may also be a larger indifferent electrode placed 119 (not shown) in the adjacent tissue.

In some embodiments, electrode 108 may contain at least two electrically conductive exposed contacts 109 configured, in use, to be placed on, in, or near a nerve. Exposed contacts 109 may be positioned, in use, transversely along the axis of a nerve.

Microprocessor

The implantable system 116, in particular the implantable device 106, may comprise a processor, for example microprocessor 113. Microprocessor 113 may be responsible for triggering the beginning and/or end of the signals delivered to the nerve (e.g., a nerve) by the at least one neural interfacing element. Optionally, microprocessor 113 may also be responsible for generating and/or controlling the parameters of the signal.

Microprocessor 113 may be configured to operate in an open-loop fashion, wherein a pre-defined signal (e.g. as described above) is delivered to the nerve at a given periodicity (or continuously) and for a given duration (or indefinitely) with or without an external trigger, and without any control or feedback mechanism. Alternatively, microprocessor 113 may be configured to operate in a closed-loop fashion, wherein a signal is applied based on a control or feedback mechanism. As described elsewhere herein, the external trigger may be an external controller 101 operable by the operator to initiate delivery of a signal.

Microprocessor 113 of the implantable system 116, in particular of the implantable device 106, may be constructed so as to generate, in use, a preconfigured and/or operator-selectable signal that is independent of any input. In some embodiments, however, microprocessor 113 is responsive to an external signal, for example information (e.g. data) pertaining to one or more physiological parameters of the subject.

Microprocessor 113 may be triggered upon receipt of a signal generated by an operator, such as a physician or the subject in which the device 116 is implanted. To that end, the implantable system 116 may be part of a system which additionally comprises an external system 118 comprising a controller 101. An example of such a system is described below with reference to FIG. 8.

External system 118 of system 100 is external the implantable system 116 and external to the subject, and comprises controller 101. Controller 101 may be used for controlling and/or externally powering implantable system 116. To this end, controller 101 may comprise a powering unit 102 and/or a programming unit 103. The external system 118 may further comprise a power transmission antenna 104 and a data transmission antenna 105, as further described below.

The controller 101 and/or microprocessor 113 may be configured to apply any one or more of the above signals to the nerve intermittently or continuously. Intermittent application of a signal involves applying the signal in an (on-off)n pattern, where n>1. For example, the stimulation may be applied for at least 1 minute, then turned off for several minutes, and then applied again, so as to ensure correct electrode placement during surgery, and validation of successful stimulation. Such intermittent application may be used for on table surgical application, for example. A continuous application may be applied as a therapeutic application, for example after the surgical placement has been achieved. In an example continuous application, the signal may be applied continuously for at least 5 days, optionally at least 7 days, before ceasing for a period (e.g. 1 day, 2 days, 3 days, 1 week, 2 weeks, 1 month), before being again applied continuously for at least 5 days, etc. Thus the signal is applied for a first time period, then stopped for a second time period, then reapplied for a third time period, then stopped for a fourth time period, etc. In such an embodiment, the first, second, third and fourth periods run sequentially and consecutively. The duration of the first, second, third and fourth time periods is independently selected. That is, the duration of each time period may be the same or different to any of the other time periods. In certain such embodiments, the duration of each of the first, second, third and fourth time periods may be any time from 1 second (s) to 10 days (d), 2 s to 7 d, 3 s to 4 d, 5 s to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h, 2 d, 3 d, 4 d, 5 d, 6 d, 7 d.

In certain embodiments, the signal is applied by controller 101 and/or microprocessor for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

Continuous application may continue indefinitely, e.g. permanently. Alternatively, the continuous application may be for a minimum period, for example the signal may be continuously applied for at least 5 days, or at least 7 days.

Whether the signal applied to the nerve is controlled by controller 101, or whether the signal is continuously applied directly by microprocessor 113, although the signal might be a series of pulses, the gaps between those pulses do not mean the signal is not continuously applied.

In certain embodiments, the signal is applied only when the subject is in a specific state e.g. only when the subject is awake, only when the subject is asleep, prior to and/or after the ingestion of food, prior to and/or after the subject undertakes exercise, during surgical placement under anesthesia, etc.

The various embodiments for timing for modulation of neural activity in the nerve can all be achieved using controller 101 in a device/system of the disclosure.

Other Components of the System Including the Implantable Device

In addition to the aforementioned electrode 108 and microprocessor 113, the implantable system 116 may comprise one or more of the following components: implantable transceiver 110; physiological sensor 111; power source 112; memory 114; and physiological data processing module 115. Additionally or alternatively, the physiological sensor 111; memory 114; and physiological data processing module 115 may be part of a sub-system external to the implantable system. Optionally, the external sub-system may be capable of communicating with the implantable system, for example wirelessly via the implantable transceiver 110.

In some embodiments, one or more of the following components may be contained in the implantable device 106: power source 112; memory 114; and a physiological data processing module 115.

The power source 112 may comprise a current source and/or a voltage source for providing the power for the signal delivered to a nerve by the electrode 108. The power source 112 may also provide power for the other components of the implantable device 106 and/or implantable system 116, such as the microprocessor 113, memory 114, and implantable transceiver 110. The power source 112 may comprise a battery, the battery may be rechargeable.

It will be appreciated that the availability of power is limited in implantable devices, and the disclosure has been devised with this constraint in mind. The implantable device 106 and/or implantable system 116 may be powered by inductive powering or a rechargeable power source.

System Including Implantable Device

With reference to FIG. 8, the implantable device 106 of the disclosure may be part of a system 110 that includes a number of subsystems, for example the implantable system 116 and the external system 118. The external system 118 may be used for powering and programming the implantable system 116 and/or the implantable device 106 through human skin and underlying tissues.

The external subsystem 118 may comprise, in addition to controller 101, one or more of: a powering unit 102, for wirelessly recharging the battery of power source 112 used to power the implantable device 106; and, a programming unit 103 configured to communicate with the implantable transceiver 110. The programming unit 103 and the implantable transceiver 110 may form a communication subsystem. In some embodiments, powering unit 102 is housed together with programing unit 103. In other embodiments, they can be housed in separate devices.

The external subsystem 118 may also comprise one or more of: power transmission antenna 104; and data transmission antenna 105. Power transmission antenna 104 may be configured for transmitting an electromagnetic field at a low frequency (e.g., from 30 kHz to 10 MHz). Data transmission antenna 105 may be configured to transmit data for programming or reprogramming the implantable device 106, and may be used in addition to the power transmission antenna 104 for transmitting an electromagnetic field at a high frequency (e.g., from 1 MHz to 10 GHz). The temperature in the skin will not increase by more than 2 degrees Celsius above the surrounding tissue during the operation of the power transmission antenna 104. The at least one antennae of the implantable transceiver 110 may be configured to receive power from the external electromagnetic field generated by power transmission antenna 104, which may be used to charge the rechargeable battery of power source 112.

The power transmission antenna 104, data transmission antenna 105, and the at least one antennae of implantable transceiver 110 have certain characteristics such a resonant frequency and a quality factor (Q). One implementation of the antenna(e) is a coil of wire with or without a ferrite core forming an inductor with a defined inductance. This inductor may be coupled with a resonating capacitor and a resistive loss to form the resonant circuit. The frequency is set to match that of the electromagnetic field generated by the power transmission antenna 105. A second antenna of the at least one antennae of implantable transceiver 110 can be used in implantable system 116 for data reception and transmission from/to the external system 118. If more than one antenna is used in the implantable system 116, these antennae are rotated 30 degrees from one another to achieve a better degree of power transfer efficiency during slight misalignment with the with power transmission antenna 104.

External system 118 may comprise one or more external body-worn physiological sensors 121 (not shown) to detect signals indicative of one or more physiological parameters. The signals may be transmitted to the implantable system 116 via the at least one antennae of implantable transceiver 110. Alternatively or additionally, the signals may be transmitted to the external system 116 and then to the implantable system 116 via the at least one antennae of implantable transceiver 110. As with signals indicative of one or more physiological parameters detected by the implanted physiological sensor 111, the signals indicative of one or more physiological parameters detected by the external sensor 121 may be processed by the physiological data processing module 115 to determine the one or more physiological parameters and/or stored in memory 114 to operate the implantable system 116 in a closed-loop fashion. The physiological parameters of the subject determined via signals received from the external sensor 121 may be used in addition to alternatively to the physiological parameters determined via signals received from the implanted physiological sensor 111.

For example, in a particular embodiment a detector external to the implantable device may include an optical detector including a camera capable of imaging the eye and determining changes in physiological parameters, in particular the physiological parameters described above. As explained above, in response to the determination of one or more of these physiological parameters, the detector may trigger delivery of signal to a nerve by the electrode 108, or may modify the parameters of the signal being delivered or a signal to be delivered to a nerve by the electrode 108 in the future.

The system 100 may include a safety protection feature that discontinues the electrical stimulation of a nerve in the following exemplary events: abnormal operation of the implantable system 116 (e.g. overvoltage); abnormal readout from an implanted physiological sensor 111 (e.g. temperature increase of more than 2 degrees Celsius or excessively high or low electrical impedance at the electrode-tissue interface); abnormal readout from an external body-worn physiological sensor 121 (not shown); or abnormal response to stimulation detected by an operator (e.g. a physician or the subject). The safety precaution feature may be implemented via controller 101 and communicated to the implantable system 116, or internally within the implantable system 116.

The external system 118 may comprise an actuator 120 (not shown) which, upon being pressed by an operator (e.g. a physician or the subject), will deliver a signal, via controller 101 and the respective communication subsystem, to trigger the microprocessor 113 of the implantable system 116 to deliver a signal to the nerve by the electrode 108.

System 100 of the disclosure, including the external system 118, but in particular implantable system 116, can be made from, or coated with, a biostable and biocompatible material. This means that the device/system is both protected from damage due to exposure to the body's tissues and also minimizes the risk that the device/system elicits an unfavorable reaction by the host (which could ultimately lead to rejection). The material used to make or coat the device/system should ideally resist the formation of biofilms. Suitable materials include, but are not limited to, poly(p-xylene) polymers (known as Parylenes) and polytetrafluoroethylene.

The implantable device 116 of the disclosure will generally weigh less than 50 g. In other examples, the implantable device 116 may weigh more, for example around 100-200 g.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the disclosure.

The term "about" in relation to a numerical value x is optional and means, for example, x+10%.

Unless otherwise indicated each embodiment as described herein may be combined with another embodiment as described herein.

The methods described herein may be performed by software in machine readable form on a tangible storage medium e.g. in the form of a computer program comprising computer program code means adapted to perform all the steps of any of the methods described herein when the program is run on a computer and where the computer program may be embodied on a computer readable medium. Examples of tangible (or non-transitory) storage media include disks, thumb drives, memory cards, etc., and do not include propagated signals. The software can be suitable for execution on a parallel processor or a serial processor such that the method steps may be carried out in any suitable order, or simultaneously. This acknowledges that firmware and software can be valuable, separately tradable commodities. It is intended to encompass software, which runs on or controls "dumb" or standard hardware, to carry out the desired functions. It is also intended to encompass software which "describes" or defines the configuration of hardware, such as HDL (hardware description language) software, as is used for designing silicon chips, or for configuring universal programmable chips, to carry out desired functions.

It will be appreciated that the modules described herein may be implemented in hardware or in software. Furthermore, the modules may be implemented at various locations throughout the system.

Those skilled in the art will realize that storage devices utilized to store program instructions can be distributed across a network. For example, a remote computer may store an example of the process described as software. A local or terminal computer may access the remote computer and download a part or all of the software to run the program. Alternatively, the local computer may download pieces of the software as needed, or execute some software instructions at the local terminal and some at the remote computer (or computer network). Those skilled in the art will also realize that by utilizing conventional techniques known to those skilled in the art that all, or a portion of the software instructions may be carried out by a dedicated circuit, such as a DSP, programmable logic array, or the like.

Any range or device value given herein may be extended or altered without losing the effect sought, as will be apparent to the skilled person. For example, a range "between" "x" and "y" may include values "x" and "y".

It will be understood that the benefits and advantages described above may relate to one embodiment or may relate to several embodiments. The embodiments are not limited to those that solve any or all of the stated problems or those that have any or all of the stated benefits and advantages.

Any reference to 'an' item refers to one or more of those items. The term 'comprising' is used herein to mean including the method blocks or elements identified, but that such blocks or elements do not comprise an exclusive list and a method or apparatus may contain additional blocks or elements.

The steps of the methods described herein may be carried out in any suitable order, or simultaneously where appropriate. Additionally, individual blocks may be deleted from any of the methods without departing from the spirit and scope of the subject matter described herein. Aspects of any of the examples described above may be combined with aspects of any of the other examples described to form further examples without losing the effect sought. Any of the module described above may be implemented in hardware or software.

It will be understood that the above description of various embodiments is given by way of example only and that various modifications may be made by those skilled in the art. Although various embodiments have been described above with a certain degree of particularity, or with reference to one or more individual embodiments, those skilled in the art could make numerous alterations to the disclosed embodiments without departing from the scope of this disclosure.

The invention claimed is:

1. A nerve stimulation system comprising:
at least one nerve interface device comprising:
at least one cuff portion having an assembled position in which the at least one cuff portion forms at least part of a passageway for receiving a nerve along a longitudinal axis passing through the passageway, and
a first ring of electrodes and a second ring of electrodes mounted on the at least one cuff portion, each of the first ring of electrodes and the second ring of electrodes comprising a plurality of electrodes, and wherein each electrode in the first ring of electrodes has a corresponding longitudinally-aligned electrode in the second ring of electrodes so as to form a plurality of pairs of electrodes spaced apart from each other along the longitudinal axis,
wherein the plurality of pairs of electrodes includes at least a first pair of electrodes and a second pair of electrodes, the first pair of electrodes mounted on the at least one cuff portion at a different circumferential position than the second pair of electrodes;
a stimulation device in electrical communication with the first pair of electrodes and the second pair of electrodes and configured to generate a first electrical signal and a second electrical signal, the first electrical signal being different from the second electrical signal with respect to at least one signal parameter selected from a group consisting of frequency, current amplitude, pulse duration, waveform shape, charge amplitude, and pulse width; and
a control system configured to cause the stimulation device to deliver the first electrical signal to the first pair of electrodes for causing a first physiological response and to deliver the second electrical signal to the second pair of electrodes for causing a second physiological response that is different from the first physiological response.

2. The nerve stimulation system of claim 1, wherein the plurality of pairs of electrodes comprise a first subset of pairs of electrodes and a second subset of pairs of electrode, wherein one or both of the electrodes in each pair of electrodes in the first subset of pairs of electrodes has a first geometry and wherein one or both of the electrodes in each pair of electrodes in the second subset of pairs of electrodes has a second geometry different from the first geometry, further wherein the first geometry comprises a length of between 0.1 mm and 2 mm, and wherein the second geometry comprises a length of between 1 mm and 5 mm, and further wherein the length of the first geometry and the length of the second geometry extend in a direction parallel to the longitudinal axis.

3. The nerve stimulation system of claim 2, wherein the control system is configured to cause the stimulation device to deliver the first electrical signal to a pair of electrodes in the first subset of pairs of electrodes for stimulating a myelinated fiber, and further wherein the control system is configured to cause the stimulation device to deliver the second electrical signal to a pair of electrodes in the second subset of pairs of electrodes for stimulating an unmyelinated fiber.

* * * * *